United States Patent [19]
Fischer

[11] 3,935,000

[45] Jan. 27, 1976

[54] HERBICIDAL MIXTURE OF A PYROZOLIUM SALT AND BENZOTHIADIOZINONE DERIVATIVE

[75] Inventor: Adolf Fischer, Mutterstadt, Germany

[73] Assignee: BASF Aktiengesellschaft, Ludwigshafen, Germany

[22] Filed: Aug. 14, 1974

[21] Appl. No.: 497,329

[30] Foreign Application Priority Data

Aug. 17, 1973 Germany............................ 2341594

[52] U.S. Cl. ......................... 71/91; 71/92; 71/105; 71/106; 71/108; 71/109; 71/110; 71/111; 71/116; 71/117; 71/121; 71/122; 71/DIG. 1
[51] Int. Cl.² ........................................ A01N 9/12
[58] Field of Search ................................ 71/91, 92

[56] References Cited
UNITED STATES PATENTS

| | | | |
|---|---|---|---|
| 3,708,277 | 1/1973 | Zeidler et al. | 71/91 |
| 3,857,692 | 12/1974 | Feeny | 71/92 |
| 3,867,403 | 2/1975 | Feeny | 71/92 |
| 3,882,142 | 5/1975 | Walworth et al. | 71/92 |

OTHER PUBLICATIONS

Fischer I, "Herbicidal Compositions, etc." (1971) CA 75, No. 7521h. (1971).
Fischer II, "Herbicidal Compositions" (1970) CA 74, No. 22060z (1971).

*Primary Examiner*—Glennon H. Hollrah
*Attorney, Agent, or Firm*—Johnston, Keil, Thompson & Shurtleff

[57] ABSTRACT

New and valuable herbicides containing compositions of different active ingredient.

4 Claims, No Drawings

HERBICIDAL MIXTURE OF A PYROZOLIUM SALT AND BENZOTHIADIOZINONE DERIVATIVE

The present invention relates to new and valuable herbicides containing compositions of different active ingredients.

It is known that pyrazolium salts, dinitrophenol derivatives, hydroxybenzonitriles, hydroxybenzaldoxime aryl ethers, benzothiadiazinone dioxides and phenoxycarboxylic acids have a herbicidal action. However, this action is not always satisfactory.

I have now found that a composition of
a. a compound of the formula

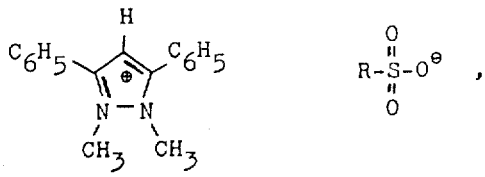

where R denotes alkoxy, or phenyl which may be substituted by halogen or lower alkyl,
and/or
b. a compound of the formula

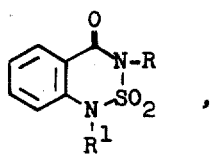

where R denotes lower alkyl and $R^1$ denotes hydrogen, or a salt thereof, e.g., salts of ammonium, sodium, potassium, lithium, calcium, magnesium, ethylamine, dimethylamine, diethylamine, diethanolamine, ethanolamine, dimethylethanolamine and trimethylamine,
and/or
c. a compound of the formula

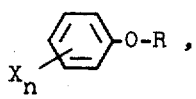

where X denotes chloro, bromo, iodo, nitro, cyano or lower alkyl, $n$ denotes one of the integers 0, 1, 2 and 3, and R denotes hydrogen, or a salt thereof, e.g., the sodium and lithium salts, R further denotes

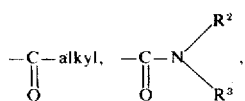

$R^2$ and $R^3$ denoting hydrogen, lower alkyl or substituted or unsubstituted aryl, R further denotes

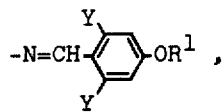

Y denoting chloro, bromo or iodo and
$R^1$ denoting lower alkyl,

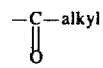

or hydrogen, or a salt thereof, e.g., the sodium salt,
and/or
d. a compound of the formula

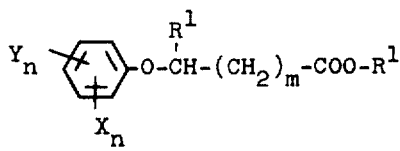

or

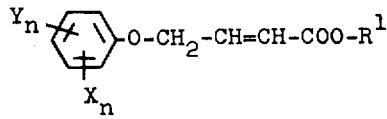

where X and Y denote chloro or methyl, $n$ denotes one of the integers 0, 1, 2 and 3, R denotes hydrogen or lower alkyl, $m$ denotes one of the integers 0, 1 and 2, and $R^1$ denotes alkyl or hydrogen, or a salt thereof, e.g., sodium, potassium, dimethylamine, diethanolamine and diethylamine, has a better herbicidal action than its individual components.

The compositions may contain one or more compounds of the formula $a$ and one or more compounds of the formulas $b$, $c$ and $d$ in a ratio by weight of from 0:1:10 to 10:1 parts in the case of 2-component mixtures, and in a ratio by weight of 0.1 to 10:0.1 to 10:0.1 to 10 parts in the case of 3-component mixtures.

The amount used of the agents according to the invention may vary and depends in essence on the type of effect to be achieved; it is generally from 0.1 to 30 (and more), preferably from 0.2 to 6, kg per hectare of active ingredient. The agents according to the invention may be used once or several times before or after planting, before sowing, and before, during or after emergence of the crop plants and unwanted plants.

The compositions are selective in *Triticum aestivum*, *Hordeum vulgare*, *Secale cereale*, *Zea mays*, *Oryza sativa*, *Pisum sativum*, *Phaseolus vulgaris*, *Solanum tuberosum*, *Glycine max*. etc.

The compositions may also be used as total herbicides on ditches, aquatic areas, railroad tracks, and barren or waste land, etc.

Preferred compositions according to the invention are: a+b, a+c, a+d, a+b+c, a+b+d, a+c+d and b+c+d.

Application may be effected for instance in the form of directly sprayable solutions, powders, suspensions, dispersions, emulsions, oil dispersions, pastes, dusts, broadcasting agents, or granules by spraying, atomizing, dusting, broadcasting of watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or mineral origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octyphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients (if desired, immediately before use (tankmix)) oils of various types, herbicides, fungicides, nematocides, insecticides, bactericides, trace elements, fertilizers, antifoams (e.g., silicones), growth regulators, antidotes and other herbicidally effective compounds such as substituted anilines, substituted aryloxycarboxylic acids and salts, esters and amides thereof
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The new compositions have a strong herbicidal action and may therefore be used as weedkillers or for controlling the growth or unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as
  Cynodon spp.
  Digitaria spp.
  Echinochloa spp.
  Setaria spp.
  Panicum spp.
  Alopecurus spp.
  Lolium spp.
  Sorghum spp.
  Agropyron spp.
  Phalaris spp.
  Apera spp.
  etc.;
  Dactylis spp.
  Avena spp.
  Bromus spp.
  Uniola spp.
  Poa spp.
  Leptochloa spp.
  Brachiaria spp.
  Eleusine spp.
  Cenchrus spp.
  Eragrostis spp.
  Phragmites communis
Cyperaceae, such as
  Carex spp.
  Cyperus spp.
  etc.;
  Eleocharis spp.
  Scirpus spp.
dicotyledonous weeds, such as
Malvaceae, e.g.
  Abutilon theoprasti
  Sida spp.
  etc.;
  Hibiscus spp.
  Malva spp.
Compositae, such as
  Ambrosia spp.
  Lactuca spp.
Senecio spp.
  Sonchus spp.
  Xanthium spp.
  Iva spp.
  Galinsoga spp.
  Taraxacum spp.
  Chrysanthemum ssp.
  Cirsium spp.
Convolvulaceae, such as
  Convolvulus spp.
  Ipomoea spp.
  etc.;
Cruciferae, such as
  Barbarea vulgaris
  Centaurea spp.
  Tussilago spp.
  Lapsana communis
  Tagetes spp.
  Erigeron spp.
  Anthemis spp.
  Mataricaria spp.
  Artemisia spp.
  Bidens spp.
  etc.;
  Cuscuta spp.
  Jaquemontia tamnifolia
  Arabidopsis thaliana
  Brassica spp.
  Capsella spp.
  Sisymbrium spp.
  Thlaspi spp.
  Sinapis arvensis
  etc.;
  Descurainia spp.
  Draba spp.
  Coronopus didymus
  Lepidium spp.
  Raphanus spp.
Geraniaceae, such as
  Erodium spp.
  etc.;
  Geranium spp.
Portulacaceae, such as
  Portulaca spp.
  etc.;
Primulaceae, such as
  Anagallis arvensis
  etc.
  Lysimachia spp.
Rubiaceae, such as
  Richardia spp.
  Galium spp.
  Diodia spp.
  etc.;
Scrophulariaceae, such as
  Linaria spp.
  Veronica spp.
  Digitalis spp.
  etc.;
Solanaceae, such as
  Physalis spp.
  Solanum spp.
  etc.;
  Nicandra spp.
  Datura spp.
Urticaceae, such as
  Urtica spp.
Violaceae, such as
  Viola spp.
  etc.;
Zygophyllaceae, such as
  Tribulus terrrestris
  etc.;
Euphorbiaceae, such as
  Mercurialis annua
  Euphorbia spp.
Umbelliferae, such as
  Daucus carota
  Aethusa cynapium
  Ammi majus
  etc.;
Commelinaceae, such as
  Commelina spp.
  etc.;
Labiatae, such as
  Lamium spp.
  etc.;
  Galeopsis spp.
Leguminosae, such as
  Medicago spp.
  Trifolium spp.
  Vicia spp.
  etc.;
  Sesbania exaltata
  Cassia spp.
  Lathyrus spp.
Plantaginaceae, such as
  Plantago spp.
  etc.;
Polygonaceae, such as
  Polygonum spp.
  Rumex spp.
  Fagopyrum spp.
  etc.;
Aizoacea, such as
  Mollugo verticillata
  etc.;
Amaranthaeceae, such as
  Amaranthus spp.
  etc.;
Boraginaceae, such as
  Amsinchkia spp.
  Myostis spp.
  etc.;
  Anchusa spp.
  Lithospermum spp.
Caryophyllaceae, such as
  Stellaria spp.
  Spergula spp.
  Saponaria spp.
  Scleranthus annuus
  Silene spp.
  Cerastium spp.
  Agrostemma githago
  etc.;
Chenopodiaceae, such as
  Chenopodium spp.
  Kochia spp.
  Salsola Kali
  Atriplex spp.
  Monolepsis nuttalliana
  etc.;
Lythraceae, such as
  Cuphea spp.
  etc.;
Oxalidaceae, such as
  Oxalis spp.
Ranunculaceae, such as
  Ranunculus spp.
  Delphinium spp.
  Adonis spp.
  etc.;
Papaveraceae, such as
  Papaver spp.
  etc.;
  Fumaria officinalis
Onagraceae, such as
  Jussiaea spp.
  etc.;
Rosaceae, such as
  Alchemillia spp.
  etc.;
  Potentilla spp.
Potamogetonaceae, such as
  Potamogeton spp.
  etc.;
Najadaceae, such as
  Najas spp.
  etc.;
Equisetaceae
  Equisetum spp.
  etc.;
Marsileaceae, such as
  Marsilea quadrifolia
  etc.;
Polypodiaceae,
  Pteridium quilinum
Alismataoeae, such as
  Alisma spp.
  etc.
  Sagittaria sagittifolia In the greenhouse and in the open, compositions of the following agents were tested on the abovementioned plants; it was ascertained that their action corresponds to that of the compositions in the examples below:

3-methyl-2,1,3-benzothiadiazinone-(4)-2,2-dioxide
3-ethyl-2,1,3-benzothiadiazinone-(4)-2,2-dioxide
3-propyl-2,1,3-benzothiadiazinone-(4)-2,2-dioxide
3-butyl-2,1,3-benzothiadiazinone-(4)-2,2-dioxide
3-isobutyl-2,1,3-benzothiadiazinone-(4)-2,2-dioxide
3-isopropyl-2,1,3-benzothiadiazinone-(4)-2,2-dioxide
3-Isopropyl-2,1,3-benzothiadiazinone-(4)-2,2-dioxide, sodium salt
3-isopropyl-2,1,3-benzothiadiazinone-(4)-2,2-dioxide, dimethylamine salt
3-isopropyl-2,1,3-benzothiadiazinone-(4)-2,2-dioxide, diethanolamine salt
3,5-dibromo-4-hydroxybenzaldoxime-O-(2',4'-dinitrophenyl)-ether
3,5-dibromo-4-hydroxybenzaldoxime-0-(2',4'-dinitrophenyl)-ether, sodium salt
3,5-dibromo-4-hydroxybenzaldoxime-0-(2'-cyano-4'-nitrophenyl)-ether
3,5-dibromo-4-hydroxybenzaldoxime-0-(2'-nitro-4'-cyanophenyl)-ether
3,5-dibromo-4-hydroxybenzaldoxime-0-(2'-cyano-4'-nitrophenyl)-ether, sodium salt
3,5-diiodo-4-hydroxybenzaldoxime-0-(2'-cyano-4'-nitrophenyl)ether
3,5-diiodo-4-hydroxybenzaldoxime-0-(2'-cyano-4'-nitrophenyl)ether, sodium salt
3,5-diiodo-4-hydroxybenzonitrile
3,5-diiodo-4-hydroxybenzonitrile, lithium salt
3,5-diiodo-4-hydroxybenzonitrile, sodium salt
3,5-dibromo-4-hydroxybenzonitrile
3,5-dibromo-4-hydroxybenzonitrile, sodium salt
3,5-dibromo-4-octanoyloxybenzonitrile
2-methyl-4,6-dinitrophenol, sodium salt
2-sec-butyl-4,6-dinitrophenyl acetate
2-tert-butyl-4,6-dinitrophenyl acetate
2-tert-butyl-5-methyl-4,6-dinitrophenyl acetate
2-isopropyl-3-methyl-4,6-dinitrophenol
2-sec-butyl-4,6-dinitrophenol, sodium salt
2-sec-amyl-4,6-dinitrophenol
2-(1-methylbutyl)-4,6-dinitrophenol
1,2-dimethyl-3,5-diphenylpyrazoliummethyl sulfate
1,2-dimethyl-3,5-diphenylpyrazolium-p-tolyl sulfonate
α-(2,4-dichlorophenoxy)-propionic acid, dimethylamine salt
α-(2,4-dichlorophenoxy)-propionic acid, sodium salt
isooctyl α-(2,4-dichlorophenoxy)-propionate
α-(2-methyl-4-chlorophenoxy)-propionic acid, dimethylamine salt
α-(2-methyl-4-chlorophenoxy)-propionic acid, diethanolamine salt
α-(2-methylphenoxy)-propionic acid, dimethylamine salt
α-(2-methylphenoxy)-propionic acid, sodium salt
isooctyl α-(2-methylphenoxy)-propionate
α-(2,4,5-trichlorophenoxy)-propionic acid, potassium salt
amyl α-(2,4,5-trichlorophenoxy)-propionate
α-(4-chlorophenoxy)-propionic acid, dimethylamine salt
α-(2-methyl-4-chlorophenoxypropionic acid, sodium salt
α-(2-methyl-4-chlorphenoxy-propionic acid, potassium salt
amyl 2,4,5-trichlorophenoxyacetate
isooctyl 2,4,5-trichlorophenoxyacetate
2,4,5-trichlorophenoxyacetic acid, diethylamine salt
2,4,5-trichlorophenoxyacetic acid, potassium salt
2,4-dichlorophenoxyacetic acid, dimethylamine salt
2,4-dichlorophenoxyacetic acid, sodium salt
isooctyl 2,4-dichlorophenoxyacetate
2-methyl-4-chlorophenoxyacetic acid, dimethylamine salt
isooctyl 2-methyl-4-chlorophenoxyacetate
4-chlorophenoxyacetic acid, dimethylamine salt
2-chlorophenoxyacetic acid, dimethylamine salt
γ-(2,4-dichlorophenoxy)-butyric acid, dimethylamine salt
isooctyl γ-(2,4-dichlorophenoxy)-butyrate
γ-(2-methyl-4-chlorophenoxy)-butyric acid, sodium salt
γ-(2,4,5-trichlorophenoxy)-butyric acid, dimethylamine salt
γ-(4-chlorophenoxy)-butyric acid
γ-(2,4-dichlorophenoxycrotonic acid, dimethylamine salt
3-isopropyl-2,1,3-benzothiadiazinone-(4)-2,2-dioxide, methylamine salt
3-isopropyl-2,1,3-benzothiadiazinone-(4)-2,2-dioxide, trimethylamine salt
3-isopropyl-2,1,3-benzothiadiazinone-(4)-2,2-dioxide, ethylamine salt
3-isopropyl-2,1,3-benzothiadiazinone-(4)-2,2-dioxide, diethylamine salt
3-isopropyl-2,1,3-benzothiadiazinone-(4)-2,2-dioxide, ethanolamine salt
3-isopropyl-2,1,3-benzothiadiazinone-(4)-2,2-dioxide, aniline salt
3-isopropyl-2,1,3-benzothiadiazinone-(4)-2,2-dioxide, pyridine salt
3-isopropyl-2,1,3-benzothiadiazinone-(4)-2,2-dioxide, phenylenediamine salt
3-isopropyl-2,1,3-benzothiadiazinone-(4)-2,2-dioxide, cyclohexylamine salt
3-isopropyl-2,1,3-benzothiadiazinone-(4)-2,2-dioxide, dodecylhexamethylenimine salt
3-isopropyl-2,1,3-benzothiadiazinone-(4)-2,2-dioxide, hydrazine salt
3-isopropyl-2,1,3-benzothiadiazinone-(4)-2,2-dioxide, magnesium salt,
3-iospropyl-2,1,3-benzothiadiazinone-(4)-2,2-dioxide, calcium salt
3-isopropyl-2,1,3-benzothiadazinone-(4)-2,2-dioxide, ammonium salt
3-isopropyl-2,1,3-benzothiadiazinone-(4)-2,2-dioxide, potassium salt
3-isopropyl-2,1,3-benzothiadiazinone-(4)-2,2-dioxide, lithium salt
3-isobutyl-2,1,3-benzothiadiazinone-(4)-2,2-dioxide, sodium salt
3-isobutyl-2,1,3-benzothiadiazinone-(4)-2,2-dioxide, dimethylamine salt
3-isobutyl-2,1,3-benzothiadiazinone-(4)-2,2-dioxide, diethanolamine salt
3-sec-butyl-2,1,3-benzothiadiazinone-(4)-2,2-dioxide, sodium salt
3-sec-butyl-2,1,3-benzothiadiazinone-(4)-2,2-dioxide, dimethylamine salt 3-sec-butyl-2,1,3-benzothiadiazinone-(4)-2,2-dioxide, diethanolamine salt
3-n-butyl-2,1,3-benzothiadiazinone-(4)-2,2-dioxide, sodium salt
3-n-butyl-2,1,3-benzothiadiazinone-(4)-2,2-dioxide, dimethylamine salt
3-n-butyl-2,1,3-benzothiadiazinone-(4)-2,2-dioxide, diethanolamine salt
3-n-propyl-2,1,3-benzothiadiazinone-(4)-2,2-dioxide, sodium salt
3-n-propyl-2,1,3-benzothiadiazinone-(4)-2,2-dioxide, dimethylamine salt
3-n-propyl-2,1,3-benzothiadiazinone-(4)-2,2-dioxide, diethanolamine salt
3-methyl-2,1,3-benzothiadiazinone-(4)-2,2-dioxide, sodium salt
3-methyl-2,1,3-benzothiadiazinone-(4)-2,2-dioxide, dimethylamine salt
3-methyl-2,1,3-benzothiadiazinone-(4)-2,2-dioxide, diethanolamine salt
3-ethyl-2,1,3benzothiadiazinone-(4)-2,2-dioxide, sodium salt amounts of the following individual active ingredients and compositions thereof as oil dispersions:

I 1,2-dimethyl-3,5-diphenylpyrazolium methyl sulfate
II 1,2-dimethyl-3,5-diphenylpyrazolium-p-tolyl sulfonate
III 3-isopropyl-2,1,3-benzothiadiazinone-(4)-2,2-dioxide
IV 3-isopropyl-2,1,3-benzothiadiazinone-(4)-2,2-dioxide, sodium salt
V 3-isopropyl-2,1,3-benzothiadiazinone-(4)-2,2-dioxide, dimethylamine salt
VI 3-isopropyl-2,1,3-benzothiadiazinone-(4)-2,2-dioxide, diethanolamine salt each of these compounds at rates of 0.5, 0.75, 1 and 1.5 kg/ha; I+III, I+IV, I+V, I+VI, II+IV and II+V each of these compositions at rates of 0.5+1, 1+0.5 and 0.75+0.75 kg/ha.

After 12 to 15 days it was ascertained that the compositions had a better herbicidal action than their components, combined with the same crop plant compatibility.

The results are given below:

| Active ingredient kg/ha | I | | | | II | | | | III | | | | IV | | | | V | | | |
|---|---|---|---|---|---|---|---|---|---|---|---|---|---|---|---|---|---|---|---|---|
| | 0.5 | 0.75 | 1 | 1.5 | 0.5 | 0.75 | 1 | 1.5 | 0.5 | 0.75 | 1 | 1.5 | 0.5 | 0.75 | 1 | 1.5 | 0.5 | 0.75 | 1 | 1.5 |
| Crop plants | | | | | | | | | | | | | | | | | | | | |
| Triticum aestivum | 0 | 0 | 0 | 0 | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 | 0 | 0 | 0 | 0 | 0 |
| Unwanted plants | | | | | | | | | | | | | | | | | | | | |
| Avena fatua | 35 | 48 | 65 | 80 | 30 | 45 | 62 | 80 | 0 | 0 | 0 | 0 | 0 | 0 | 0 | 0 | 0 | 0 | 0 | 0 |
| Galium aparine | 0 | 5 | 6 | 10 | 0 | 0 | 5 | 10 | 35 | 45 | 60 | 75 | 30 | 40 | 60 | 75 | 30 | 40 | 50 | 60 |
| Stellaria media | 5 | 8 | 10 | 14 | 0 | 5 | 8 | 12 | 30 | 40 | 60 | 70 | 20 | 30 | 55 | 70 | 20 | 35 | 50 | 70 |

0 = no damage
100 = complete destruction

| Active ingredient | IV | | | | I + III | | | | I + IV | | | | I + V | | | | I + VI | | | | II + IV | | | | II + V | | | |
|---|---|---|---|---|---|---|---|---|---|---|---|---|---|---|---|---|---|---|---|---|---|---|---|---|---|---|---|---|
| | 0.5 | 0.75 | 1 | 1.5 | 0.5 1 | 1 0.5 | 0.75 0.75 | 0.5 1 | 1 0.5 | 0.75 0.75 | 0.5 1 | 1 0.5 | 0.75 0.75 | 0.5 1 | 1 0.5 | 0.75 0.75 | 0.5 1 | 1 0.5 | 0.75 0.75 | 0.5 1 | 1 0.5 | 0.75 0.75 |
| Crop plants: | | | | | | | | | | | | | | | | | | | | | | |
| Triticum aestivum | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Unwanted plants: | | | | | | | | | | | | | | | | | | | | | | |
| Avena fatua | 0 | 0 | 0 | 0 | 84 | 97 | 90 | 85 | 100 | 90 | 96 | 98 | 93 | 82 | 100 | 96 | 78 | 95 | 87 | 75 | 95 | 90 |
| Galium aparine | 35 | 45 | 65 | 80 | 98 | 85 | 94 | 97 | 80 | 90 | 98 | 80 | 90 | 100 | 85 | 95 | 97 | 80 | 83 | 90 | 76 | 84 |
| Stellaria media | 20 | 40 | 60 | 85 | 95 | 82 | 86 | 93 | 76 | 80 | 100 | 75 | 80 | 98 | 77 | 90 | 90 | 70 | 78 | 94 | 74 | 85 |

0 = no damage
100 = complete destruction 3-ethyl-2,1,3-benzothiadiazinone-(4)-2,2-dioxide, dimethylamine salt
3-ethyl-2,1,3-benzothiadiazinone-(4)-2,2-dioxide, diethanolamine salt
3-sec-butyl-2,1,3-benzothiadiazinone-(4)-2,2-dioxide
3,5-dibromo-4-acetyloxybenzaldoxime-0-(2'-cyano-4'-nitrophenyl)ether
3,5-dibromo-4-propionyloxybenzaldoxime-0-(2'-cyano-4'-nitrophenyl)-ether
3,5-dibromo-4-phenylcarbamoyloxybenzaldoxime-0-(2'-cyano-4'-nitrophenyl)-ether
3,5-dibromo-4-isopropylcarbamoyloxybenzaldoxime-0-(2'-cyano-4'-nitrophenyl)-ether

EXAMPLE 1

In the greenhouse, various plants were treated at a growth height of from 2 to 21 cm with the following

EXAMPLE 2

In the greenhouse, various plants were treated at a growth height of from 3 to 25 cm with the following amounts of the following individual active ingredients and compositions thereof as emulsions:

I 1,2-dimethyl-3,5-diphenylpyrazolium methyl sulfate
II 1,2-dimethyl-3,5-diphenylpyrazolium-p-tolyl sulfonate
III 3-isopropyl-2,1,3-benzothiadiazinone-(4)-2,2-dioxide
IV 3-isopropyl-2,1,3-benzothiadiazinone-(4)-2,2-dioxide, sodium salt
V 3-isopropyl-2,1,3-benzothiadiazinone-(4)-2,2-dioxide, dimethylamine salt
VI 3-isopropyl-2,1,3-benzothiadiazinone-(4)-2,2-dioxide, diethanolamine salt each of these compounds at rates of 0.5, 1.5, 2.5 and 3 kg/ha; I+III, I+IV, I+V, I+VI, II+IV and II+V
each of these compositions at rates of 2.5+0.5, 0.5+2.5 and 1.5+1.5 kg/ha.

After 14 to 18 days it was ascertained that the compositions had a better herbicidal action than their components, combined with the same crop plant compatibility.

The results are given below:

V 3-isopropyl-2,1,3-benzothiadiazinone-(4)-2,2-dioxide, dimethylamine salt
VII 2-sec-butyl-4,6-dinitrophenyl acetate
VIII 3,5-diiodo-4-hydroxybenzonitrile
IX 3,5-dibromo-4-hydroxybenzaldoxime-O-(2',4'-dinitrophenyl)-ether
X 3,5-dibromo-4-hydroxybenzaldoxime-O-(2'-cyano-4'-nitrophenyl)-ether, sodium salt each of these compounds at rates of 0.25, 1 and 1.5 kg/ha;

| Active ingredient kg/ha | I | | | | II | | | | III | | | | IV | | | | V | | | |
|---|---|---|---|---|---|---|---|---|---|---|---|---|---|---|---|---|---|---|---|---|
| | 0.5 | 1.5 | 2.5 | 3 | 0.5 | 1.5 | 2.5 | 3 | 0.5 | 1.5 | 2.5 | 3 | 0.5 | 1.5 | 2.5 | 3 | 0.5 | 1.5 | 2.5 | 3 |
| Crop plants: | | | | | | | | | | | | | | | | | | | | |
| Triticum aestivum | 0 | 0 | 0 | 5 | 0 | 0 | 5 | 10 | 0 | 0 | 0 | 0 | 0 | 0 | 0 | 0 | 0 | 0 | 0 | 0 |
| Hordeum vulgare | 0 | 0 | 0 | 10 | 0 | 0 | 7 | 10 | 0 | 0 | 0 | 0 | 0 | 0 | 0 | 0 | 0 | 0 | 0 | 0 |
| Secale cereale | 0 | 0 | 0 | 12 | 0 | 0 | 10 | 15 | 0 | 0 | 0 | 0 | 0 | 0 | 0 | 0 | 0 | 0 | 0 | 0 |
| Unwanted plants: | | | | | | | | | | | | | | | | | | | | |
| Avena fatua | 35 | 80 | 95 | 100 | 30 | 80 | 90 | 100 | 0 | 0 | 0 | 0 | 0 | 0 | 0 | 0 | 0 | 0 | 0 | 0 |
| Galium aparine | 0 | 10 | 15 | 26 | 0 | 10 | 16 | 23 | 35 | 75 | 90 | 95 | 30 | 75 | 90 | 95 | 30 | 60 | 90 | 100 |
| Stellaria media | 5 | 14 | 20 | 30 | 0 | 12 | 20 | 30 | 30 | 70 | 86 | 95 | 20 | 70 | 90 | 94 | 20 | 70 | 93 | 95 |

0 = no damage
100 = complete destruction

| Active ingredient kg/ha | VI | | | | I+III | | | I+IV | | | I+V | | |
|---|---|---|---|---|---|---|---|---|---|---|---|---|---|
| | | | | | 2.5 | 0.5 | 1.5 | 2.5 | 0.5 | 1.5 | 2.5 | 0.5 | 1.5 |
| | 0.5 | 1.5 | 2.5 | 3 | 0.5 | 2.5 | 1.5 | 0.5 | 2.5 | 1.5 | 0.5 | 2.5 | 1.5 |
| Crop plants: | | | | | | | | | | | | | |
| Triticum aestivum | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 |
| Unwanted plants: | | | | | | | | | | | | | |
| Avena fatua | 0 | 0 | 0 | 0 | 100 | 85 | 100 | 100 | 86 | 100 | 100 | 88 | 100 |
| Galium aparine | 35 | 80 | 90 | 95 | 97 | 100 | 100 | 94 | 100 | 100 | 96 | 100 | 100 |
| Stellaria media | 20 | 85 | 100 | 100 | 98 | 100 | 100 | 90 | 100 | 100 | 90 | 100 | 100 |

| Active ingredient kg/ha | I+VI | | | II+IV | | | II+V | | |
|---|---|---|---|---|---|---|---|---|---|
| | 2.5 | 0.5 | 1.5 | 2.5 | 0.5 | 1.5 | 2.5 | 0.3 | 1.5 |
| | 0.5 | 2.5 | 1.5 | 0.5 | 2.5 | 1.5 | 0.5 | 2.5 | 1.5 |
| Crop plants: | | | | | | | | | |
| Triticum aestivum | 0 | 0 | 0 | 5 | 0 | 0 | 5 | 0 | 0 |
| Hordeum vulgare | 0 | 0 | 0 | 7 | 0 | 0 | 7 | 0 | 0 |
| Secale cereale | 0 | 0 | 0 | 10 | 0 | 0 | 10 | 0 | 0 |
| Unwanted plants: | | | | | | | | | |
| Avena fatua | 100 | 85 | 100 | 100 | 82 | 100 | 100 | 80 | 100 |
| Galium aparine | 97 | 100 | 100 | 95 | 100 | 100 | 95 | 100 | 100 |
| Stellaria media | 90 | 100 | 100 | 87 | 100 | 100 | 80 | 100 | 100 |

0 = no damage
100 = complete destruction

EXAMPLE 3

In the greenhouse, various plants were treated at a growth height of from 2 to 21 cm with the following amounts of the following inndividual active ingredients and compositions thereof as dispersions:

I 1,2-dimethyl-3,5-diphenylpyrazolium methyl sulfate
II 1,2-dimethyl-3,5-diphenylpyrazolium-p-tolyl sulfonate I+V+VII, I+V+VIII, I+V+IX, II+V+VII, II+V+VIII, II+V+IX and I+V+X each of these compositions at rates of 1+0.25+0.25, 0.25+1+0.25 and 0.25+0.25+1 kg/ha.

After 12 to 16 days it was ascertained that the compositions had a better herbicidal action than their components, combined with the same crop plant compatibility.

The results are given below:

| Active ingredient kg/ha | I | | | II | | | V | | | VII | | | VIII | | | IX | | | X | | |
|---|---|---|---|---|---|---|---|---|---|---|---|---|---|---|---|---|---|---|---|---|---|
| | 0.25 | 1 | 1.5 | 0.25 | 1 | 1.5 | 0.25 | 1 | 1.5 | 0.25 | 1 | 1.5 | 0.25 | 1 | 1.5 | 0.25 | 1 | 1.5 | 0.25 | 1 | 1.5 |
| Crop plants | | | | | | | | | | | | | | | | | | | | | |
| Triticum aestivum | 0 | 0 | 0 | 0 | 0 | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 | 0 | 0 | 0 | 0 | 0 | 0 |
| unwanted plants | | | | | | | | | | | | | | | | | | | | | |
| Avena fatua | 20 | 65 | 80 | 18 | 62 | 80 | 0 | 0 | 0 | 0 | 0 | 5 | 0 | 0 | 0 | 0 | 0 | 0 | 0 | 0 | 0 |
| Galium aparine | 0 | 6 | 10 | 0 | 5 | 10 | 20 | 50 | 60 | 18 | 40 | 50 | 15 | 30 | 60 | 20 | 50 | 60 | 25 | 95 | 100 |

-continued

| Active ingredient kg/ha | I | | | II | | | V | | | VII | | | VIII | | | IX | | | X | | |
|---|---|---|---|---|---|---|---|---|---|---|---|---|---|---|---|---|---|---|---|---|---|
| | 0.25 | 1 | 1.5 | 0.25 | 1 | 1.5 | 0.25 | 1 | 1.5 | 0.25 | 1 | 1.5 | 0.25 | 1 | 1.5 | 0.25 | 1 | 1.5 | 0.25 | 1 | 1.5 |
| Stellaria media | 0 | 10 | 14 | 0 | 8 | 12 | 25 | 50 | 75 | 20 | 40 | 45 | 25 | 45 | 70 | 15 | 48 | 70 | 20 | 80 | 100 |

0 = damage
100 = complete destruction

| Active ingredient kg/ha | I+V+VII | | | I+V+VIII | | | I+V+IX | | | I+V+X | | | II+V+VII | | |
|---|---|---|---|---|---|---|---|---|---|---|---|---|---|---|---|
| | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 0.25<br>0.25<br>1 | 0.25<br>1<br>0.25 | 1<br>0.25<br>0.25 |
| Crop plants | | | | | | | | | | | | | | | |
| Triticum aestivum | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 |
| Unwanted plants | | | | | | | | | | | | | | | |
| Avena fatua | 80 | 75 | 82 | 78 | 98 | 70 | 100 | 80 | 80 | 100 | 82 | 85 | 77 | 70 | 100 |
| Galium aparine | 85 | 98 | 100 | 100 | 100 | 93 | 90 | 100 | 100 | 98 | 100 | 100 | 80 | 100 | 85 |
| Stellaria media | 90 | 96 | 100 | 100 | 100 | 100 | 96 | 97 | 100 | 100 | 100 | 100 | 96 | 100 | 100 |

| Active ingredient kg/ha a.S. | II+V+VII | | | II+V+IX | | |
|---|---|---|---|---|---|---|
| | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | |
| Triticum aestivum | 0 | 0 | 0 | 0 | 0 | 0 |
| Hordeum vulgare | 0 | 0 | 0 | 0 | 0 | 0 |
| Secale cereale | 0 | 0 | 0 | 0 | 0 | 0 |
| Unwanted plants | | | | | | |
| Avena fatua | 98 | 70 | 74 | 100 | 78 | 73 |
| Galium aparine | 84 | 100 | 90 | 98 | 100 | 100 |
| Stellaria media | 97 | 100 | 100 | 97 | 100 | 100 |

0 = no damage
100 = complete destruction

EXAMPLE 4

In the open, various plants were treated at a growth height of from 2 to 18 cm with the following amounts of the following individual active ingredients and compositions thereof as emulsions:

I 1,2-dimethyl-3,5-diphenylpyrazolium methyl sulfate
III 3-isopropyl-2,1,3-benzothiadiazinone-(4)-2,2-dioxide
IV 3-isopropyl-2,1,3-benzothiadiazinone-(4)-2,2-dioxide, sodium salt
V 3-isopropyl-2,1,3-benzothiadiazinone-(4)-2,2-dioxide, dimethylamine salt
VI 3-isopropyl-2,1,3-benzothiadiazinone-(4)-2,2-dioxide, diethanolamine salt
XI α-(2-methyl-4-chlorophenoxy)-propionic acid, dimethylamine salt
XII α-(2,4-dichlorophenoxy)-propionic acid, dimethylamine salt
XIII α-(2,4,5-trichlorophenoxy)-propionic acid, potassium salt
XIV 2-methyl-4-chlorophenoxyacetic acid, dimethylamine salt
XV 2,4-dichlorophenoxyacetic acid, diethanolamine salt
XVI 2,4,5-trichlorophenoxyacetic acid, potassium salt each of these compounds at rates of 0.5, 1,2 and 3 kg/ha; III+I+XVI, IV+I+XIII, V+I+XI, V+I+XII, V+I+XIV and VI+I+XV each of these compositions of rate of I+I+I, 0.5+2+0.5, 2+0.5+0.5 and 0.5+0.5+2 kg/ha.

After 14 to 17 days it was ascertained that the compositions had a better herbicidal action than their components, combined with the same crop plant compatibility.

The results are given below:

| Active ingredient kg/ha | I | | | | III | | | | IV | | | | V | | | | VI | | | |
|---|---|---|---|---|---|---|---|---|---|---|---|---|---|---|---|---|---|---|---|---|
| | 0.5 | 1 | 2 | 3 | 0.5 | 1 | 2 | 3 | 0.5 | 1 | 2 | 3 | 0.5 | 1 | 2 | 3 | 0.5 | 1 | 2 | 3 |
| Crop plants | | | | | | | | | | | | | | | | | | | | |
| Triticum aestivum | 0 | 0 | 0 | 5 | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 10 | 0 | 0 | 0 | 0 | 0 | 0 | 0 | 0 | 0 | 0 | 0 | 0 | 0 | 0 | 0 | 0 |
| Secale cereale | 0 | 0 | 0 | 12 | 0 | 0 | 0 | 0 | 0 | 0 | 0 | 0 | 0 | 0 | 0 | 0 | 0 | 0 | 0 | 0 |
| Unwanted plants | | | | | | | | | | | | | | | | | | | | |
| Avena fatua | 35 | 65 | 90 | 100 | 0 | 0 | 0 | 0 | 0 | 0 | 0 | 0 | 0 | 0 | 0 | 0 | 0 | 0 | 0 | 0 |
| Galium aparine | 0 | 6 | 13 | 26 | 35 | 60 | 85 | 95 | 30 | 60 | 85 | 95 | 30 | 50 | 86 | 100 | 35 | 65 | 85 | 95 |
| Stellaria media | 5 | 10 | 16 | 30 | 30 | 60 | 82 | 95 | 20 | 55 | 80 | 92 | 20 | 50 | 90 | 95 | 20 | 60 | 95 | 100 |

0 = damage
100 = complete destruction

| Active ingredient kg/ha | XI | | | | XII | | | | XIII | | | | XIV | | | | XV | | | |
|---|---|---|---|---|---|---|---|---|---|---|---|---|---|---|---|---|---|---|---|---|
| | 0.5 | 1 | 2 | 3 | 0.5 | 1 | 2 | 3 | 0.5 | 1 | 2 | 3 | 0.5 | 1 | 2 | 3 | 0.5 | 1 | 2 | 3 |
| Crop plants | | | | | | | | | | | | | | | | | | | | |

-continued

| Active Ingredient kg/ha | XI | | | | XII | | | | XIII | | | | XIV | | | | XV | | | |
|---|---|---|---|---|---|---|---|---|---|---|---|---|---|---|---|---|---|---|---|---|
| | 0.5 | 1 | 2 | 3 | 0.5 | 1 | 2 | 3 | 0.5 | 1 | 2 | 3 | 0.5 | 1 | 2 | 3 | 0.5 | 1 | 2 | 3 |
| Triticum aestivum | 0 | 0 | 0 | 0 | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 | 0 | 0 | 0 | 0 | 0 |
| Unwanted plants | | | | | | | | | | | | | | | | | | | | |
| Avena fatua | 0 | 0 | 5 | 15 | 0 | 0 | 5 | 15 | 0 | 0 | 10 | 30 | 0 | 0 | 0 | 10 | 0 | 0 | 0 | 10 |
| Galium aparine | 30 | 50 | 85 | 100 | 20 | 65 | 80 | 100 | 40 | 57 | 95 | 100 | 10 | 20 | 27 | 30 | 10 | 20 | 30 | 40 |
| Stellaria media | 35 | 45 | 90 | 100 | 0 | 10 | 20 | 40 | 45 | 60 | 95 | 100 | 15 | 20 | 38 | 45 | 5 | 10 | 28 | 40 |

0 = no damage
100 = complete destruction

| Active ingredient kg/ha | XVI | | | | III+I+XVI | | | | IV+I+XII | | | |
|---|---|---|---|---|---|---|---|---|---|---|---|---|
| | 0.5 | 1 | 2 | 3 | 1<br>1<br>1 | 0.5<br>2<br>0.5 | 2<br>0.5<br>0.5 | 0.5<br>0.5<br>2 | 1<br>1<br>1 | 0.25<br>2<br>0.5 | 2<br>0.5<br>0.5 | 0.5<br>0.5<br>2 |
| Crop plants | | | | | | | | | | | | |
| Triticum aestivum | 0 | 0 | 7 | 15 | 0 | 0 | 0 | 7 | 0 | 0 | 0 | 0 |
| Hordeum vulgare | 0 | 0 | 10 | 30 | 0 | 0 | 0 | 10 | 0 | 0 | 0 | 0 |
| Secale cereale | 0 | 0 | 10 | 17 | 0 | 0 | 0 | 10 | 0 | 0 | 0 | 0 |
| Unwanted plants | | | | | | | | | | | | |
| Avena fatua | 0 | 0 | 0 | 20 | 100 | 100 | 70 | 70 | 100 | 100 | 70 | 80 |
| Galium aparine | 30 | 60 | 80 | 100 | 100 | 100 | 100 | 100 | 100 | 100 | 100 | 100 |
| Stellaria media | 35 | 50 | 90 | 100 | 100 | 100 | 100 | 100 | 100 | 100 | 100 | 100 |

| Active ingredient kg/ha | V+I+XI | | | | V+I+XII | | | |
|---|---|---|---|---|---|---|---|---|
| | 1<br>1<br>1 | 0.5<br>2<br>0.5 | 2<br>0.5<br>0.5 | 0.5<br>0.5<br>2 | 1<br>1<br>1 | 0.5<br>2<br>0.5 | 2<br>0.5<br>0.5 | 0.5<br>0.5<br>2 |
| Crop plants | | | | | | | | |
| Triticum aestivum | 0 | 0 | 0 | 0 | 0 | 0 | 0 | 0 |
| Hordeum vulgare | 0 | 0 | 0 | 0 | 0 | 0 | 0 | 0 |
| Secale cereale | 0 | 0 | 0 | 0 | 0 | 0 | 0 | 0 |
| Unwanted plants | | | | | | | | |
| Avena fatua | 100 | 100 | 72 | 76 | 100 | 100 | 71 | 76 |
| Galium aparine | 100 | 100 | 100 | 100 | 100 | 100 | 100 | 100 |
| Stellaria media | 100 | 100 | 100 | 100 | 100 | 72 | 100 | 100 |

0 = no damage
100 = complete destruction

| Active ingredient kg/ha | V+I+XIV | | | | VI+I+XV | | | |
|---|---|---|---|---|---|---|---|---|
| | 1<br>1<br>1 | 0.5<br>2<br>0.5 | 2<br>0.5<br>0.5 | 0.5<br>0.5<br>2 | 1<br>1<br>1 | 0.5<br>2<br>0.5 | 2<br>0.5<br>0.5 | 0.5<br>0.5<br>2 |
| Crop plants | | | | | | | | |
| Triticum aestivum | 0 | 0 | 0 | 0 | 0 | 0 | 0 | 0 |
| Hordeum vulgare | 0 | 0 | 0 | 0 | 0 | 0 | 0 | 0 |
| Secale cereale | 0 | 0 | 0 | 0 | 0 | 0 | 0 | 0 |
| Unwanted plants | | | | | | | | |
| Avena fatua | 100 | 100 | 70 | 70 | 100 | 100 | 70 | 71 |
| Galium aparine | 100 | 90 | 100 | 92 | 100 | 92 | 100 | 100 |
| Stellaria media | 100 | 88 | 100 | 100 | 100 | 78 | 100 | 87 |

0 = no damage
100 = complete destruction

EXAMPLE 5

In the greenhouse, various plants were treated at a growth height of from 2 to 18 cm with the following amounts of the following individual active ingredients and compositions thereof as solutions:

I 1,2-dimethyl-3,5-diphenylpyrazolium methyl sulfate
VII 2-sec-butyl-4,6-dinitrophenyl acetate
XII α-(2,4-dichlorophenoxy)-propionic acid, dimethylamine salt each of these compounds at rates of 0.5, 1 and 2 kg/ha; I+VII+XII at rates of 1+0.5+0.5, 0.5+1+0.5 and 0.5+0.5+1 kg/ha.

After 14 to 16 days it was ascertained that the compositions had a better herbicidal action than their components, combined with the same crop plant compatibility.

The results are given below:

| Active ingredient kg/ha | I | | | VII | | | XII | | | I+VII+XII | | |
|---|---|---|---|---|---|---|---|---|---|---|---|---|
| | 0.5 | 1 | 2 | 0.5 | 1 | 2 | 0.5 | 1 | 2 | 1<br>0.5<br>0.5 | 0.5<br>1<br>0.5 | 0.5<br>0.5<br>1 |
| Crop plants | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |

| Active ingredient | I | | | VII | | | XII | | | I+VII+XII | | |
|---|---|---|---|---|---|---|---|---|---|---|---|---|
| kg/ha | 0.5 | 1 | 2 | 0.5 | 1 | 2 | 0.5 | 1 | 2 | 0.5 / 0.5 / 0.5 | 0.5 / 1 / 0.5 | 0.5 / 0.5 / 1 |
| Secale cereale | 0 | 0 | 0 | 0 | 0 | 0 | 0 | 0 | 0 | 0 | 0 | 0 |
| Unwanted plants | | | | | | | | | | | | |
| Avena fatua | 35 | 65 | 90 | 0 | 0 | 10 | 0 | 0 | 5 | 100 | 69 | 70 |
| Galium aparine | 0 | 6 | 13 | 25 | 40 | 55 | 20 | 65 | 80 | 88 | 97 | 100 |
| Stellaria media | 5 | 10 | 16 | 20 | 40 | 50 | 0 | 10 | 20 | 66 | 80 | 70 |

0 = no damage
100 = complete destruction

EXAMPLE 6

In the greenhouse, various plants were treated at a growth height of from 2 to 24 cm with the following amounts of the following individual active ingredients and compositions thereof as emulsions:

I 1,2-dimethyl-3,5-diphenylpyrazolium methyl sulfate
VII 2-sec-butyl-4,6-dinitrophenyl acetate
VIII 3,5-diiodo-4-hydroxybenzonitrile, lithium salt
IX 3,5-dibromo-4-hydroxybenzaldoxime-O-(2',4'-dinitrophenyl)ether, sodium salt
X 3,5-dibromo-4-hydroxybenzaldoxime-O-(2'-cyano-4'-nitrophenyl)-ether, sodium salt
XI α-(2-methyl-4-chlorophenoxy)-propionic acid, dimethylamine salt
XII α-(2,4-dichlorophenoxy)-propionic acid, dimethylamine salt
XIII α-(2,4,5-trichlorophenoxy)-propionic acid, isooctyl ester
XIV 2-methyl-4-chlorophenoxyacetic acid, dimethylamine salt
XV 2,4-dichlorophenoxyacetic acid, dimethylamine salt
XVI 2,4,5-trichlorophenoxyacetic acid, isooctyl ester
XVII γ-(2,4-dichlorophenoxy)-butyric acid, dimethylamine salt
XVIII 3,5-dibromo-4-hydroxybenzonitrile, sodium salt each of these compounds at rates of 0.5, 0.75, 1 and 1.5 kg/ha; I+VII, I+VIII, I+IX, I+X, I+XI, I+XII, I+XIII, I+XIV, I+XV, I+XVI, I+XVII and I+XVIII
each of these compositions at rates of 0.5+1, 1+0.5 and 0.75+0.75 kg/ha.

After 12 to 15 days it was ascertained that the compositions had a better herbicidal action than their components, combined with the same crop plant compatibility.

The results are given below:

| Active ingredient | I+XIV | | | I+XV | | | I+XVI | | | I+XVII | | | I+XVIII | | |
|---|---|---|---|---|---|---|---|---|---|---|---|---|---|---|---|
| kg/ha | 0.5/1 | 1/0.5 | 0.75/0.75 | 0.5/1 | 1/0.5 | 0.75/0.75 | 0.5/1 | 1/0.5 | 0.75/0.75 | 0.5/1 | 1/0.5 | 0.75/0.75 | 0.5/1 | 1/0.5 | 0.75/0.75 |
| Crop plants | | | | | | | | | | | | | | | |
| Triticum aestivum | 0 | 0 | 0 | 0 | 0 | 0 | 0 | 0 | 0 | 0 | 0 | 0 | 10 | 5 | 7 |
| Hordeum vulgare | 0 | 0 | 0 | 0 | 0 | 0 | 0 | 0 | 0 | 0 | 0 | 0 | 5 | 0 | 0 |
| Secale cereale | 0 | 0 | 0 | 0 | 0 | 0 | 0 | 0 | 0 | 0 | 0 | 0 | 8 | 0 | 0 |
| Unwanted plants | | | | | | | | | | | | | | | |
| Avena fatua | 82 | 100 | 88 | 80 | 100 | 89 | 82 | 100 | 88 | 81 | 100 | 88 | 82 | 100 | 89 |
| Galium aparine | 60 | 58 | 62 | 60 | 56 | 62 | 98 | 80 | 90 | 58 | 59 | 61 | 92 | 69 | 85 |
| Stellaria media | 64 | 65 | 58 | 57 | 55 | 51 | 66 | 60 | 58 | 54 | 56 | 50 | 100 | 80 | 94 |

0 = no damage
100 = complete destruction

| Active ingredient | I+IX | | | I+X | | | I+XI | | | I+XII | | | I+XIII | | |
|---|---|---|---|---|---|---|---|---|---|---|---|---|---|---|---|
| kg/ha | 0.5/1 | 1/0.5 | 0.75/0.75 | 0.5/1 | 1/0.5 | 0.75/0.75 | 0.5/1 | 1/0.5 | 0.75/0.75 | 0.5/1 | 1/0.5 | 0.75/0.75 | 0.5/1 | 1/0.5 | 0.75/0.75 |
| Crop plants | | | | | | | | | | | | | | | |
| Triticum aestivum | 0 | 0 | 0 | 0 | 0 | 0 | 0 | 0 | 0 | 0 | 0 | 0 | 5 | 0 | 0 |
| Hordeum vulgare | 0 | 0 | 0 | 0 | 0 | 0 | 0 | 0 | 0 | 0 | 0 | 0 | 7 | 0 | 0 |
| Secale cereale | 0 | 0 | 0 | 0 | 0 | 0 | 0 | 0 | 0 | 0 | 0 | 0 | 10 | 0 | 0 |
| Unwanted plants | | | | | | | | | | | | | | | |
| Avena fatua | 80 | 100 | 88 | 80 | 100 | 88 | 81 | 100 | 89 | 80 | 100 | 87 | 83 | 100 | 88 |
| Galium aparine | 90 | 76 | 90 | 100 | 80 | 94 | 90 | 76 | 90 | 100 | 95 | 100 | 100 | 87 | 93 |
| Stellaria media | 93 | 80 | 75 | 100 | 84 | 79 | 91 | 80 | 79 | 100 | 77 | 80 | 100 | 85 | 90 |

0 = no damage
100 = complete destruction

| Active ingredient | XVI | | | XVII | | | | XVIII | | | | I+VII | | | I+VIII | | |
|---|---|---|---|---|---|---|---|---|---|---|---|---|---|---|---|---|---|
| kg/ha | 0.5 | 0.5 | 1 | 1.5 | 0.5 | 0.75 | 1 | 1.5 | 0.5 | 0.75 | 1 | 1.5 | 0.5/1 | 1/0.5 | 0.75/0.75 | 0.5/1 | 1/0.5 | 0.75/0.75 |
| Crop plants | | | | | | | | | | | | | | | | | | |
| Triticum aestivum | 0 | 0 | 0 | 0 | 0 | 0 | 0 | 5 | 7 | 10 | 12 | 0 | 0 | 0 | 10 | 0 | 0 |
| Hordeum vulgare | 0 | 0 | 0 | 5 | 0 | 0 | 0 | 0 | 0 | 5 | 6 | 0 | 0 | 0 | 10 | 0 | 0 |
| Secale cereale | 0 | 0 | 0 | 7 | 0 | 0 | 0 | 0 | 0 | 8 | 10 | 0 | 0 | 0 | 20 | 0 | 0 |
| Unwanted plants | | | | | | | | | | | | | | | | | | |
| Avena fatua | 0 | 0 | 0 | 0 | 0 | 0 | 0 | 0 | 0 | 0 | 0 | 87 | 100 | 98 | 81 | 100 | 88 |
| Galium aparine | 30 | 45 | 60 | 80 | 12 | 15 | 18 | 25 | 20 | 40 | 50 | 67 | 86 | 76 | 86 | 98 | 76 | 100 |

-continued

| Active ingredient | XVI | | | | XVII | | | | XVIII | | | | I+VII | | | | I+VIII | | |
|---|---|---|---|---|---|---|---|---|---|---|---|---|---|---|---|---|---|---|---|
| kg/ha | 0.5 | 0.5 | 1 | 1.5 | 0.5 | 0.75 | 1 | 1.5 | 0.5 | 0.75 | 1 | 1.5 | 0.5 | 1 | 0.75 | 0.5 | 1 | 0.75 |
| | | | | | | | | | | | | | 1 | 0.5 | 0.75 | 1 | 0.5 | 0.75 |
| Stellaria media | 10 | 16 | 20 | 36 | 5 | 6 | 8 | 15 | 25 | 54 | 70 | 78 | 100 | 90 | 91 | 99 | 82 | 89 |

0 = no damage
100 = complete destruction

| Active ingredient kg/ha | XI | | | | XII | | | | XIII | | | | XIV | | | | XV | | | |
|---|---|---|---|---|---|---|---|---|---|---|---|---|---|---|---|---|---|---|---|---|
| | 0.5 | 0.75 | 1 | 1.5 | 0.5 | 0.75 | 1 | 1.5 | 0.5 | 0.75 | 1 | 1.5 | 0.5 | 0.75 | 1 | 1.5 | 0.5 | 0.75 | 1 | 1.5 |
| Crop plants | | | | | | | | | | | | | | | | | | | | |
| Triticum aestivum | 0 | 0 | 0 | 0 | 0 | 0 | 0 | 0 | 0 | 5 | 10 | 0 | 0 | 0 | 0 | 0 | 0 | 0 | 0 | 0 |
| Galium aparine | 0 | 0 | 0 | 0 | 0 | 0 | 0 | 0 | 0 | 7 | 10 | 0 | 0 | 0 | 0 | 0 | 0 | 0 | 0 | 0 |
| Stellaria media | 0 | 0 | 0 | 0 | 0 | 0 | 0 | 0 | 0 | 10 | 12 | 0 | 0 | 0 | 0 | 0 | 0 | 0 | 0 | 0 |
| Unwanted plants | | | | | | | | | | | | | | | | | | | | |
| Avena fatua | 0 | 0 | 0 | 0 | 0 | 0 | 5 | 0 | 0 | 4 | 10 | 0 | 0 | 0 | 0 | 0 | 0 | 0 | 0 | 0 |
| Galium aparine | 30 | 45 | 50 | 70 | 50 | 58 | 65 | 75 | 40 | 48 | 60 | 85 | 10 | 15 | 20 | 25 | 10 | 15 | 20 | 25 |
| Stellaria media | 30 | 40 | 45 | 70 | 25 | 40 | 55 | 75 | 30 | 50 | 65 | 85 | 15 | 18 | 20 | 35 | 5 | 8 | 10 | 20 |

0 = no damage
100 = complete destruction

| Active Ingredient kg/ha | I | | | | VII | | | | VVIII | | | | IX | | | | X | | | |
|---|---|---|---|---|---|---|---|---|---|---|---|---|---|---|---|---|---|---|---|---|
| | 0.5 | 0.75 | 1 | 1.5 | 0.5 | 0.75 | 1 | 1.5 | 0.5 | 0.75 | 1 | 1.5 | 0.5 | 0.75 | 1 | 1.5 | 0.5 | 0.75 | 1 | 1.5 |
| Crop plants | | | | | | | | | | | | | | | | | | | | |
| Triticum aestivum | 0 | 0 | 0 | 0 | 0 | 0 | 0 | 0 | 0 | 10 | 20 | 0 | 0 | 0 | 10 | 0 | 0 | 0 | 0 | 0 |
| Hordeum vulgare | 0 | 0 | 0 | 0 | 0 | 0 | 0 | 0 | 0 | 10 | 10 | 0 | 0 | 0 | 15 | 0 | 0 | 0 | 0 | 0 |
| Secale cereale | 0 | 0 | 0 | 0 | 0 | 0 | 0 | 0 | 0 | 20 | 20 | 0 | 0 | 0 | 10 | 0 | 0 | 0 | 0 | 0 |
| Unwanted plants | | | | | | | | | | | | | | | | | | | | |
| Avena fatua | 35 | 48 | 65 | 80 | 0 | 10 | 12 | 15 | 0 | 0 | 0 | 0 | 0 | 0 | 0 | 0 | 0 | 0 | 0 | 0 |
| Galium aparine | 0 | 5 | 6 | 10 | 30 | 40 | 46 | 50 | 30 | 56 | 60 | 70 | 30 | 45 | 50 | 60 | 30 | 45 | 90 | 100 |
| Stellaria media | 5 | 0 | 10 | 14 | 40 | 50 | 60 | 75 | 30 | 48 | 55 | 80 | 30 | 35 | 48 | 70 | 30 | 35 | 80 | 100 |

0 = no damage
100 = complete destruction

EXAMPLE 7

In the greenhouse, various plants were treated at a growth height of from 2 to 20 cm with the following amounts of the following individual active ingredients and compositions thereof as dispersions, emulsions, solutions and tankmixes:

I 1,2-dimethyl-3,5-diphenylpyrazolium methyl sulfate
III 3-isopropyl-2,1,3-benzothiadiazinone-(4)-2,2-dioxide
IV 3-isopropyl-2,1,3-benzothiadiazinone-(4)-2,2-dioxide, sodium salt
V 3-isopropyl-2,1,3-benzothiadiazinone-(4)-2,2-dioxide, dimethylamine salt
VI 3-isopropyl-2,1,3-benzothiadiazinone-(4)-2,2-dioxide, diethanolamine salt
VII 2-sec-butyl-4,6-dinitrophenyl acetate
VIII 3,5-diiodo-4-hydroxybenzonitrile, sodium salt
IX 3,5-dibromo-4-hydroxybenzaldoxime-O-(2',4'-dinitrophenyl)ether
X 3,5-dibromo-4-hydroxybenzaldoxime-O-(2'-cyano-4'-nitrophenyl)-ether, sodium salt
XI α-(2-methyl-4-chlorophenoxy)-propionic acid, dimethylamine salt
XII α-(2,4-dichlorophenoxy)-propionic acid, sodium salt
XIII α-(2,4,5-trichlorophenoxy)-propionic acid, potassium salt
XIV 2-methyl-4-chlorophenoxyacetic acid, dimethylamine salt
XV 2,4-dichlorophenoxyacetic acid, dimethylamine salt
XVI 2,4,5-trichlorophenoxyacetic acid, potassium salt
XVII γ-(2,4-dichlorophenoxy)-butyric acid, dimethylamine salt
XVIII 3,5-dibromo-4-hydroxybenzonitrile, sodium salt each of these compounds at rates of 0.25, 1 and 1.5 kg/ha;

I + III + VII, I + III + VIII, I + III + IX, I + III + X, I + III + XI, I + III + XII, I + III + XIII, I + III + XIV, I + III + XV, I + III + XVII, I + IV + XI, I + IV + XII, I + IV + XIV, I + IV + XV, I + IV + XVI, I + IV + XVII, I + V + VII, I + V + VIII, I + V + XVIII, I + V IX, I + V + X, I + V + XV, I + V + XVI, I + V + XVII, I + VI + VII, I + VI + VIII, I + VI + IX, I + VI + X, I + VI + XI, I + VI + VIII, I + VII + XI, I + VII + XII, I + VII + XIII, I + VII + XIV, I + VII + XV, I + VII + XVI, I + VII + XVII, I + VIII + XI, I + VIII + XII, I + VIII + XIII, I + VIII + XIV, I + VIII + XV, I + VIII + XVI, I + VIII + XVII, I + XVIII + XI, I + XVIII + XII, I + XVIII + XIII, I + XVIII + XIV, I + XVIII + XV, I + XVIII + XV, I + XVIII + XVII, I + IX + XI, I + IX + XII, I + IX + XIII, I + IX + XIV, I + IX + XV, I + IX + XV, I + IX + XVII, I + X + XI, I + IX + XII, I + IX + XIII, I + IX + XIV, I + IX + XV, I + IX + XV, I + IX + XVII, I + X + XI, I + X + XII, I + X + XIII, I + X + XIV, I + X + XV, I + X + XVI, I + X + XVII, III + VII + XI, III + VII + XII, III + VII + XIII, III + VII + XIV, III + VII + XV, III + VII + XV, III + VII + XVII, III + VII + XI, III + VIII + XVII, III + VIII + XIII, III + VIII + XIV, III + VIII + XV, III + VIII + XVI, III + VIII + XVII, III + IX + XI, III + IX + XII, III + IX + XIII, III + IX + XIV, III + IX + XV, III + IX + XV, III + IX + XVII, III + X + XI, III + X + XII, III + X + XIII, III + X + XIV, III + X + XV, III + X + XVI, III + X + XVII, IV + VIII + XI, IV + VIII + XII, IV + VIII + XIII, IV + VIII + XIV, IV + VIII + XV, IV + VIII + XVI, IV + VIII + XVII, IV +

IX + XI, IV + IX + XII, IV + IX + XIII, IV + IX + XIV, IV + IX + XV, IV + IX + XVI, IV + IX + XVII, IV + X + XI, IV + X + XII, IV + X + XIII, IV + X + XIV, IV + X + XV, IV + X + XVI, IV + X + XVII, V + VII + XI, V + VII + XII, V + VII + XIII, V + VII + XIV, V + VII + XV, V + VII + XVI, V + VII + XVII, V + VIII + XI, V + VIII + XII, V + VIII + XIII, V + VIII + XIII, V + VIII + XV, V + VIII + XV, V + VIII + XVII, V + IX + XI, V + IX + XII, V + IX + XIII, V + IX + XIV, V + IX + XV, V + IX + XVI, V + IX + XVII, III + XVIII + XI, III + XVIII + XII, III + XVIII + XIII, III + XVIII + XIV, III + XVIII + XV, III + XVIII + XVI, III + XVIII + XVII, IV + VII + XI, IV + VII + XII, IV + VII + XIII, IV + VII + XIV, IV + VII + XV, IV + VII + XVI, IV + VII + XVII, III + XVIII + XI, III + XVIII + XII, III + XVIII + XIV, III + XVII + XV, III + XVIII + XVI, III + XVII + XVII, V + X + XI, V + X + XII, V + X + XIII, V + X + XIV, V + X + XV, V + X + XVI, V + X + XVII each of these compositions at rates of 1+0.25+0.25, 0.25+1+0.25 and 0.25+0.25+1 kg/ha.

After 12 to 15 days it was ascertained that the compositions had a better herbicidal action than their components, combined with the same crop plant compatibility.

The results are given below:

| Active ingredient kg/ha | I | | | III | | | IV | | | V | | | VI | | | VII | | | VIII | | |
|---|---|---|---|---|---|---|---|---|---|---|---|---|---|---|---|---|---|---|---|---|---|
| | 0.25 | 1 | 1.5 | 0.25 | 1 | 1.5 | 0.25 | 1 | 1.5 | 0.25 | 1 | 1.5 | 0.25 | 1 | 1.5 | 0.25 | 1 | 1.5 | 0.25 | 1 | 1.5 |
| Crop plants | | | | | | | | | | | | | | | | | | | | | |
| Triticum aestivum | 0 | 0 | 0 | 0 | 0 | 0 | 0 | 0 | 0 | 0 | 0 | 0 | 0 | 0 | 0 | 0 | 0 | 0 | 0 | 10 | 20 |
| Hordeum vulgare | 0 | 0 | 0 | 0 | 0 | 0 | 0 | 0 | 0 | 0 | 0 | 0 | 0 | 0 | 0 | 0 | 0 | 0 | 0 | 10 | 10 |
| Secale cereale | 0 | 0 | 0 | 0 | 0 | 0 | 0 | 0 | 0 | 0 | 0 | 0 | 0 | 0 | 0 | 0 | 0 | 5 | 0 | 20 | 20 |
| Unwanted plants | | | | | | | | | | | | | | | | | | | | | |
| Avena fatua | 20 | 65 | 80 | 0 | 0 | 0 | 0 | 0 | 0 | 0 | 0 | 0 | 0 | 0 | 0 | 0 | 10 | 15 | 0 | 0 | 0 |
| Galium aparine | 0 | 6 | 10 | 15 | 60 | 75 | 15 | 66 | 75 | 20 | 50 | 60 | 25 | 65 | 80 | 18 | 40 | 50 | 15 | 60 | 70 |
| Stellaria media | 0 | 10 | 14 | 25 | 60 | 70 | 10 | 65 | 70 | 25 | 50 | 70 | 10 | 60 | 85 | 20 | 60 | 75 | 25 | 55 | 80 |

0 = no damage
100 = complete destruction

| Active ingredient kg/ha | IX | | | X | | | XI | | | XII | | | XIII | | | XIV | | | XV | | |
|---|---|---|---|---|---|---|---|---|---|---|---|---|---|---|---|---|---|---|---|---|---|
| | 0.25 | 1 | 1.5 | 0.25 | 1 | 1.5 | 0.25 | 1 | 1.5 | 0.25 | 1 | 1.5 | 0.25 | 1 | 1.5 | 0.25 | 1 | 1.5 | 0.25 | 1 | 1.5 |
| Crop plants | | | | | | | | | | | | | | | | | | | | | |
| Triticum aestivum | 0 | 0 | 10 | 0 | 0 | 0 | 0 | 0 | 0 | 0 | 0 | 0 | 0 | 5 | 10 | 0 | 0 | 0 | 0 | 0 | 0 |
| Hordeum vulgare | 0 | 0 | 15 | 0 | 0 | 0 | 0 | 0 | 0 | 0 | 0 | 0 | 0 | 7 | 10 | 0 | 0 | 0 | 0 | 0 | 0 |
| Secale cereale | 0 | 0 | 10 | 0 | 0 | 5 | 0 | 0 | 0 | 0 | 0 | 0 | 0 | 10 | 12 | 0 | 0 | 0 | 0 | 0 | 0 |
| Unwanted plants | | | | | | | | | | | | | | | | | | | | | |
| Avena fatua | 0 | 0 | 0 | 0 | 0 | 0 | 0 | 0 | 0 | 0 | 0 | 5 | 0 | 4 | 10 | 0 | 0 | 0 | 0 | 0 | 0 |
| Galium aparine | 20 | 50 | 60 | 25 | 90 | 100 | 15 | 50 | 70 | 10 | 65 | 75 | 20 | 60 | 85 | 5 | 20 | 25 | 5 | 20 | 25 |
| Stellaria media | 15 | 48 | 70 | 20 | 80 | 100 | 20 | 45 | 70 | 15 | 55 | 75 | 15 | 65 | 85 | 10 | 20 | 35 | 3 | 10 | 20 |

0 = no damage
100 = complete destruction

| Active ingredient kg/ha | XVI | | | XVII | | | XVIII | | | I+III+VII | | | I+III+VIII | | | I+III+XVIII | | |
|---|---|---|---|---|---|---|---|---|---|---|---|---|---|---|---|---|---|---|
| | 0.25 | 1 | 1.5 | 0.25 | 1 | 1.5 | 0.25 | 1 | 1.5 | 1 / 0.25 / 0.25 | 0.25 / 1 / 0.25 | 0.25 / 0.25 / 1 | 1 / 0.25 / 0.25 | 0.25 / 1 / 0.25 | 0.25 / 0.25 / 1 | 1 / 0.25 / 0.25 | 0.25 / 1 / 0.25 | 0.25 / 0.25 / 1 |
| Crop plants | | | | | | | | | | | | | | | | | | |
| Triticum aestivum | 0 | 0 | 0 | 0 | 0 | 0 | 0 | 10 | 12 | 0 | 0 | 0 | 0 | 0 | 10 | 0 | 0 | 10 |
| Hordeum vulgare | 0 | 0 | 5 | 0 | 0 | 0 | 0 | 5 | 6 | 0 | 0 | 0 | 0 | 0 | 10 | 0 | 0 | 5 |
| Secale cereale | 0 | 0 | 7 | 0 | 0 | 0 | 0 | 8 | 10 | 0 | 0 | 0 | 0 | 0 | 20 | 0 | 0 | 8 |
| Unwanted plants | | | | | | | | | | | | | | | | | | |
| Avena fatua | 0 | 0 | 0 | 0 | 0 | 0 | 0 | 0 | 0 | 100 | 65 | 76 | 93 | 64 | 60 | 90 | 62 | 60 |
| Galium aparine | 15 | 60 | 80 | 9 | 18 | 25 | 10 | 50 | 67 | 79 | 100 | 95 | 80 | 100 | 100 | 75 | 100 | 100 |
| Stellaria media | 5 | 20 | 36 | 2 | 8 | 15 | 15 | 54 | 78 | 95 | 100 | 100 | 100 | 100 | 100 | 87 | 100 | 100 |

0 = no damage
100 = complete destruction

| Active ingredient kg/ha | I+III+IX | | | I+V+VII | | | I+V+XIII | | | I+VI+XIV | | | I+VI+XV | | | I+VI+XVI | | |
|---|---|---|---|---|---|---|---|---|---|---|---|---|---|---|---|---|---|---|
| | 1 / 0.25 / 0.25 | 0.25 / 1 / 0.25 | 0.25 / 0.25 / 1 | 1 / 0.25 / 0.25 | 0.25 / 1 / 0.25 | 0.25 / 0.25 / 1 | 1 / 0.25 / 0.25 | 0.25 / 1 / 0.25 | 0.25 / 0.25 / 1 | 1 / 0.25 / 0.25 | 0.25 / 1 / 0.25 | 0.25 / 0.25 / 1 | 1 / 0.25 / 0.25 | 0.25 / 1 / 0.25 | 0.25 / 0.25 / 1 | 1 / 0.25 / 0.25 | 0.25 / 1 / 0.25 | 0.25 / 0.25 / 1 |
| Crop plants | | | | | | | | | | | | | | | | | | |
| Triticum aestivum | 0 | 0 | 0 | 0 | 0 | 0 | 0 | 0 | 5 | 0 | 0 | 0 | 0 | 0 | 0 | 0 | 0 | 0 |
| Hordeum vulgare | 0 | 0 | 0 | 0 | 0 | 0 | 0 | 0 | 7 | 0 | 0 | 0 | 0 | 0 | 0 | 0 | 0 | 0 |
| Secale cereale | 0 | 0 | 0 | 0 | 0 | 0 | 0 | 0 | 10 | 0 | 0 | 0 | 0 | 0 | 0 | 0 | 0 | 0 |
| Unwanted plants | | | | | | | | | | | | | | | | | | |
| Avena fatua | 100 | 67 | 75 | 98 | 65 | 54 | 100 | 63 | 67 | 100 | 66 | 57 | 99 | 62 | 60 | 100 | 61 | 60 |
| Galium aparine | 80 | 100 | 98 | 84 | 100 | 98 | 100 | 100 | 100 | 80 | 100 | 82 | 81 | 100 | 85 | 86 | 100 | 100 |

| Active ingredient kg/ha | I+III+IX 1 / 0.25 / 0.25 | | 0.25 / 1 / 0.25 | 0.25 / 0.25 / 1 | I+V+VII 1 / 0.25 / 0.25 | 0.25 / 1 / 0.25 | 0.25 / 0.25 / 1 | I+V+XIII 1 / 0.25 / 0.25 | 0.25 / 1 / 0.25 | 0.25 / 0.25 / 1 | I+VI+XIV 1 / 0.25 / 0.25 | 0.25 / 1 / 0.25 | 0.25 / 0.25 / 1 | I+VI+XV 1 / 0.25 / 0.25 | 0.25 / 1 / 0.25 | 0.25 / 0.25 / 1 | I+VI+XVI 1 / 0.25 / 0.25 | 0.25 / 1 / 0.25 | 0.25 / 0.25 / 1 |
|---|---|---|---|---|---|---|---|---|---|---|---|---|---|---|---|---|---|---|---|
| Stellaria media | 93 | | 100 | 100 | 95 | 100 | 100 | 100 | 100 | 100 | 75 | 100 | 77 | 69 | 100 | 66 | 70 | 100 | 77 |

0 = no damage
100 = complete destruction

| Active ingredient kg/ha | I+IV+XI 1 / 0.25 / 0.25 | 0.25 / 1 / 0.25 | 0.25 / 0.25 / 1 | I+IV+XII 1 / 0.25 / 0.25 | 0.25 / 1 / 0.25 | 0.25 / 0.25 / 1 | I+IV+XIV 1 / 0.25 / 0.25 | 0.25 / 1 / 0.25 | 0.25 / 0.25 / 1 | I+IV+XV 1 / 0.25 / 0.25 | 0.25 / 1 / 0.25 | 0.25 / 0.25 / 1 | I+IV+XVI 1 / 0.25 / 0.25 | 0.25 / 1 / 0.25 | 0.25 / 0.25 / 1 |
|---|---|---|---|---|---|---|---|---|---|---|---|---|---|---|---|
| Crop plants | | | | | | | | | | | | | | | |
| Triticum aestivum | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 |
| Unwanted plants | | | | | | | | | | | | | | | |
| Avena fatua | 100 | 66 | 73 | 96 | 64 | 69 | 91 | 60 | 61 | 88 | 56 | 59 | 94 | 63 | 59 |
| Galium aparine | 75 | 100 | 98 | 72 | 100 | 100 | 70 | 94 | 77 | 70 | 100 | 76 | 77 | 100 | 100 |
| Stellaria media | 79 | 100 | 92 | 74 | 100 | 96 | 72 | 98 | 70 | 65 | 100 | 68 | 70 | 97 | 74 |

0 = no damage
100 = complete destruction

| Active ingredient kg/ha | I+IV+XVII 1 / 0.25 / 0.25 | 0.25 / 1 / 0.25 | 0.25 / 0.25 / 1 | I+V+VII 1 / 0.25 / 0.25 | 0.25 / 1 / 0.25 | 0.25 / 0.25 / 1 | I+III+X 1 / 0.25 / 0.25 | 0.25 / 1 / 0.25 | 0.25 / 0.25 / 1 | I+III+XI 1 / 0.25 / 0.25 | 0.25 / 1 / 0.25 | 0.25 / 0.25 / 1 | I+III+XII 1 / 0.25 / 0.25 | 0.25 / 1 / 0.25 | 0.25 / 0.25 / 1 |
|---|---|---|---|---|---|---|---|---|---|---|---|---|---|---|---|
| Crop plants | | | | | | | | | | | | | | | |
| Triticum aestivum | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 |
| Unwanted plants | | | | | | | | | | | | | | | |
| Avena fatua | 86 | 53 | 55 | 98 | 64 | 73 | 100 | 70 | 75 | 95 | 64 | 67 | 97 | 66 | 70 |
| Galium aparine | 73 | 100 | 80 | 100 | 100 | 97 | 95 | 100 | 100 | 80 | 100 | 100 | 75 | 100 | 100 |
| Stellaria media | 65 | 100 | 70 | 100 | 100 | 100 | 100 | 100 | 100 | 97 | 100 | 100 | 90 | 100 | 100 |

0 = no damage
100 = complete destruction

| Active ingredient kg/ha | I+III+XIII 1 / 0.25 / 0.25 | 0.25 / 1 / 0.25 | 0.25 / 0.25 / 1 | I+III+XIV 1 / 0.25 / 0.25 | 0.25 / 1 / 0.25 | 0.25 / 0.25 / 1 | I+III+XV 1 / 0.25 / 0.25 | 0.25 / 1 / 0.25 | 0.25 / 0.25 / 1 | I+III+XVII 1 / 0.25 / 0.25 | 0.25 / 1 / 0.25 | 0.25 / 0.25 / 1 | I+V+VIII 1 / 0.25 / 0.25 | 0.25 / 1 / 0.25 | 0.25 / 0.25 / 1 |
|---|---|---|---|---|---|---|---|---|---|---|---|---|---|---|---|
| Crop plants | | | | | | | | | | | | | | | |
| Triticum aestivum | 0 | 0 | 5 | 0 | 0 | 0 | 0 | 0 | 0 | 0 | 0 | 0 | 0 | 0 | 10 |
| Hordeum vulgare | 0 | 0 | 7 | 0 | 0 | 0 | 0 | 0 | 0 | 0 | 0 | 0 | 0 | 0 | 10 |
| Secale cereale | 0 | 0 | 10 | 0 | 0 | 0 | 0 | 0 | 0 | 0 | 0 | 0 | 0 | 0 | 20 |
| Unwanted plants | | | | | | | | | | | | | | | |
| Avena fatua | 100 | 65 | 70 | 92 | 60 | 63 | 90 | 57 | 60 | 88 | 55 | 57 | 92 | 64 | 60 |
| Galium aparine | 83 | 100 | 100 | 70 | 94 | 75 | 70 | 100 | 74 | 72 | 100 | 80 | 80 | 100 | 100 |
| Stellaria media | 90 | 100 | 100 | 82 | 100 | 80 | 77 | 100 | 75 | 75 | 90 | 80 | 97 | 100 | 100 |

0 = no damage
100 = complete destruction

| Active ingredient kg/ha | I+V+XVIII 1 / 0.25 / 0.25 | 0.25 / 1 / 0.25 | 0.25 / 0.25 / 1 | I+V+IX 1 / 0.25 / 0.25 | 0.25 / 1 / 0.25 | 0.25 / 0.25 / 1 | I+V+X 1 / 0.25 / 0.25 | 0.25 / .1 / 0.25 | 0.25 / 0.25 / 1 | I+V+XV 1 / 0.25 / 0.25 | 0.25 / 1 / 0.25 | 0.25 / 0.25 / 1 | I+V+XVI 1 / 0.25 / 0.25 | 0.25 / 1 / 0.25 | 0.25 / 0.25 / 1 |
|---|---|---|---|---|---|---|---|---|---|---|---|---|---|---|---|
| Crop plants | | | | | | | | | | | | | | | |
| Triticum aestivum | 0 | 0 | 10 | 0 | 0 | 0 | 0 | 0 | 0 | 0 | 0 | 0 | 0 | 0 | 0 |
| Hordeum vulgare | 0 | 0 | 5 | 0 | 0 | 0 | 0 | 0 | 0 | 0 | 0 | 0 | 0 | 0 | 0 |
| Secale cereale | 0 | 0 | 8 | 0 | 0 | 0 | 0 | 0 | 0 | 0 | 0 | 0 | 0 | 0 | 0 |
| Unwanted plants | | | | | | | | | | | | | | | |
| Avena fatua | 89 | 63 | 58 | 98 | 64 | 73 | 92 | 63 | 72 | 88 | 65 | 60 | 95 | 63 | 60 |
| Galium aparine | 80 | 98 | 100 | 100 | 100 | 100 | 88 | 100 | 100 | 68 | 93 | 80 | 80 | 100 | 100 |
| Stellaria media | 92 | 100 | 100 | 100 | 98 | 100 | 94 | 97 | 100 | 75 | 90 | 72 | 77 | 100 | 89 |

0 = no damage
100 = complete destruction

| Active ingredient | I+V+XVII | | | I+VI+VII | | | I+VI+VIII | | | I+VI+XVIII | | | I+VI+IX | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | | | | | | | | | | |
| Triticum aestivum | 0 | 0 | 0 | 0 | 0 | 0 | 0 | 0 | 10 | 0 | 0 | 10 | 0 | 0 | 0 |
| Hordeum vulgare | 0 | 0 | 0 | 0 | 0 | 0 | 0 | 0 | 10 | 0 | 0 | 5 | 0 | 0 | 0 |
| Secale cereale | 0 | 0 | 0 | 0 | 0 | 0 | 0 | 0 | 20 | 0 | 0 | 8 | 0 | 0 | 0 |
| Unwanted plants | | | | | | | | | | | | | | | |
| Avena fatua | 87 | 54 | 56 | 95 | 61 | 70 | 91 | 61 | 58 | 87 | 59 | 57 | 96 | 63 | 71 |
| Galium aparine | 78 | 100 | 79 | 90 | 100 | 100 | 85 | 100 | 100 | 80 | 100 | 100 | 90 | 100 | 100 |
| Stellaria media | 75 | 98 | 70 | 78 | 100 | 100 | 87 | 100 | 97 | 86 | 100 | 97 | 77 | 100 | 96 |

0 = no damage
100 = complete destruction

| Active ingredient | I+VI+X | | | I+VI+XI | | | I+VI+XIII | | | I+VII+XI | | | I+VII+XII | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | | | | | | | | | | |
| Triticum aestivum | 0 | 0 | 0 | 0 | 0 | 0 | 0 | 0 | 5 | 0 | 0 | 0 | 0 | 0 | 0 |
| Hordeum vulgare | 0 | 0 | 0 | 0 | 0 | 0 | 0 | 0 | 7 | 0 | 0 | 0 | 0 | 0 | 0 |
| Secale cereale | 0 | 0 | 0 | 0 | 0 | 0 | 0 | 0 | 10 | 0 | 0 | 0 | 0 | 0 | 0 |
| Unwanted plants | | | | | | | | | | | | | | | |
| Avena fatua | 98 | 91 | 75 | 92 | 61 | 63 | 97 | 62 | 68 | 94 | 63 | 66 | 95 | 64 | 68 |
| Galium aparine | 100 | 100 | 100 | 83 | 100 | 100 | 90 | 100 | 100 | 80 | 95 | 100 | 72 | 87 | 100 |
| Stellaria media | 86 | 100 | 100 | 85 | 100 | 97 | 80 | 100 | 100 | 88 | 100 | 98 | 86 | 100 | 100 |

0 = no damage
100 = complete destruction

| Active ingredient | I+VII+XIII | | | II+VII+XIV | | | I+VII+XV | | | I+VII+XVI | | | I+VII+XVII | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | | | | | | | | | | |
| Triticum aestivum | 0 | 0 | 5 | 0 | 0 | 0 | 0 | 0 | 0 | 0 | 0 | 0 | 0 | 0 | 0 |
| Hordeum vulgare | 0 | 0 | 7 | 0 | 0 | 0 | 0 | 0 | 0 | 0 | 0 | 0 | 0 | 0 | 0 |
| Secale cereale | 0 | 0 | 10 | 0 | 0 | 0 | 0 | 0 | 0 | 0 | 0 | 0 | 0 | 0 | 0 |
| Unwanted plants | | | | | | | | | | | | | | | |
| Avena fatua | 98 | 65 | 70 | 93 | 59 | 63 | 90 | 56 | 61 | 96 | 64 | 60 | 89 | 55 | 58 |
| Galium aparine | 85 | 96 | 100 | 70 | 87 | 80 | 70 | 84 | 75 | 80 | 93 | 100 | 70 | 87 | 74 |
| Stellaria media | 85 | 100 | 100 | 70 | 100 | 78 | 72 | 96 | 74 | 77 | 98 | 78 | 75 | 95 | 72 |

0 = no damage
100 = complete destruction

| Active ingredient | I+VIII+XI | | | I+VIII+XII | | | I+VIII+XIII | | | I+VIII+XIV | | | I+VIII+XV | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | | | | | | | | | | |
| Triticum aestivum | 0 | 10 | 0 | 0 | 10 | 0 | 0 | 10 | 5 | 0 | 10 | 0 | 0 | 10 | 0 |
| Hordeum vulgare | 0 | 10 | 0 | 0 | 10 | 0 | 0 | 10 | 7 | 0 | 10 | 0 | 0 | 10 | 0 |
| Secale cereale | 0 | 20 | 0 | 0 | 20 | 0 | 0 | 20 | 10 | 0 | 20 | 0 | 0 | 20 | 0 |
| Unwanted plants | | | | | | | | | | | | | | | |
| Avena fatua | 96 | 63 | 70 | 93 | 61 | 66 | 96 | 61 | 66 | 93 | 61 | 64 | 90 | 57 | 60 |
| Galium aparine | 73 | 100 | 97 | 73 | 100 | 100 | 80 | 100 | 100 | 70 | 96 | 76 | 70 | 97 | 77 |
| Stellaria media | 97 | 100 | 100 | 90 | 100 | 100 | 90 | 100 | 100 | 84 | 98 | 87 | 80 | 96 | 74 |

0 = no damage
100 = complete destruction

| Active ingredient | I+VIII+VI | | | I+VIII+XVII | | | I+XVIII+XI | | | I+XVIII+XII | | | I+XVIII+XIII | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Corp plants | | | | | | | | | | | | | | | |
| Triticum aestivum | 0 | 10 | 0 | 0 | 10 | 0 | 0 | 10 | 0 | 0 | 10 | 0 | 0 | 10 | 5 |
| Hordeum vulgare | 0 | 10 | 0 | 0 | 10 | 0 | 0 | 5 | 0 | 0 | 5 | 0 | 0 | 5 | 7 |
| Secale cereale | 0 | 20 | 0 | 0 | 20 | 0 | 0 | 8 | 0 | 0 | 8 | 0 | 0 | 8 | 10 |
| Unwanted plants | | | | | | | | | | | | | | | |
| Avena fatua | 94 | 62 | 58 | 87 | 54 | 56 | 92 | 61 | 64 | 93 | 60 | 65 | 95 | 62 | 69 |
| Galium aparine | 75 | 100 | 100 | 71 | 100 | 70 | 70 | 97 | 96 | 70 | 98 | 100 | 80 | 100 | 100 |

-continued

| Active ingredient kg/ha | I+VIII+VI | | | I+VIII+XVII | | | I+XVIII+XI | | | I+XVIII+XII | | | I+XVIII+XIII | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| *Stellaria media* | 80 | 95 | 85 | 79 | 95 | 76 | 80 | 100 | 95 | 78 | 100 | 100 | 85 | 100 | 100 |

0 = no damage
100 = complete destruction

| Active ingredient kg/ha | I+XVIII+XIV | | | I+XVIII+XV | | | I+XVII+XVI | | | I+XVII+XVII | | | I+IX+XI | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Corp plants | | | | | | | | | | | | | | | |
| *Triticum aestivum* | 0 | 10 | 0 | 0 | 10 | 0 | 0 | 10 | 0 | 0 | 10 | 0 | 0 | 0 | 0 |
| *Hordeum vulgare* | 0 | 5 | 0 | 0 | 5 | 0 | 0 | 5 | 0 | 0 | 5 | 0 | 0 | 0 | 0 |
| *Secale cereale* | 0 | 8 | 0 | 0 | 8 | 0 | 0 | 8 | 0 | 0 | 8 | 0 | 0 | 0 | 0 |
| Unwanted plants | | | | | | | | | | | | | | | |
| *Avena fatua* | 90 | 57 | 60 | 90 | 55 | 61 | 94 | 63 | 60 | 88 | 53 | 56 | 92 | 60 | 64 |
| *Galium aparine* | 65 | 90 | 70 | 64 | 90 | 68 | 77 | 100 | 100 | 70 | 98 | 68 | 80 | 100 | 100 |
| *Stellaria media* | 72 | 96 | 78 | 73 | 95 | 75 | 75 | 98 | 78 | 70 | 96 | 66 | 84 | 100 | 100 |

0 = no damage
100 = complete destruction

| Active ingredient kg/ha | I+IX+XII | | | I+IX+XIII | | | I+IX+XIV | | | I+IX+XV | | | I+IX+XVI | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| *Triticum aestivum* | 0 | 0 | 0 | 0 | 0 | 5 | 0 | 0 | 0 | 0 | 0 | 0 | 0 | 0 | 0 |
| *Hordeum vulgare* | 0 | 0 | 0 | 0 | 0 | 7 | 0 | 0 | 0 | 0 | 0 | 0 | 0 | 0 | 0 |
| *Secale cereale* | 0 | 0 | 0 | 0 | 0 | 10 | 0 | 0 | 0 | 0 | 0 | 0 | 0 | 0 | 0 |
| Unwanted plants | | | | | | | | | | | | | | | |
| *Avena fatua* | 95 | 61 | 66 | 96 | 64 | 69 | 91 | 60 | 63 | 89 | 55 | 61 | 95 | 62 | 60 |
| *Galium aparine* | 75 | 97 | 100 | 85 | 100 | 100 | 68 | 90 | 77 | 70 | 90 | 77 | 80 | 97 | 100 |
| *Stellaria media* | 77 | 98 | 100 | 84 | 100 | 100 | 73 | 96 | 73 | 70 | 88 | 67 | 70 | 90 | 73 |

0 = no damage
100 = complete destruction

| Active ingredient kg/ha | I+IX+XVII | | | I+X+XI | | | I+X+XII | | | I+X+XIII | | | I+X+XIV | | | |
|---|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 | |
| | 0.25 | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 0.25 | 1 | 0.25 | 0.25 | 1 | 0.25 | 0.25 | 1 | 0.25 | 0.25 | 1 | 0.25 | 1 | | |
| Crop plants | | | | | | | | | | | | | | | | |
| *Triticum aestivum* | 0 | 0 | 0 | 0 | 0 | 0 | 0 | 0 | 0 | 0 | 0 | 5 | 0 | 0 | 0 | |
| *Hordeum vulgare* | 0 | 0 | 0 | 0 | 0 | 0 | 0 | 0 | 0 | 0 | 0 | 7 | 0 | 0 | 0 | |
| *Secale cereale* | 0 | 0 | 0 | 0 | 0 | 0 | 0 | 0 | 0 | 0 | 0 | 10 | 0 | 0 | 0 | |
| Unwanted plants | | | | | | | | | | | | | | | | |
| *Avena fatua* | 90 | 56 | 59 | 95 | 63 | 67 | 96 | 65 | 68 | 97 | 63 | 70 | 94 | 58 | 62 | |
| *Galium aparine* | 71 | 95 | 80 | 90 | 100 | 100 | 85 | 100 | 100 | 90 | 100 | 100 | 80 | 100 | 90 | |
| *Stellaria media* | 70 | 87 | 64 | 93 | 100 | 100 | 84 | 100 | 100 | 90 | 100 | 100 | 86 | 100 | 87 | |

0 = no damage
100 = complete destruction

| Active ingredient kg/ha | I+X+XV | | | I+X+XVI | | | I+X+XVII | | | III+VII+XI | | | III+VII+XII | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| *Triticum aestivum* | 0 | 0 | 0 | 0 | 0 | 0 | 0 | 0 | 0 | 0 | 0 | 0 | 0 | 0 | 0 |
| *Hordeum vulgare* | 0 | 0 | 0 | 0 | 0 | 0 | 0 | 0 | 0 | 0 | 0 | 0 | 0 | 0 | 0 |
| *Secale cereale* | 0 | 0 | 0 | 0 | 0 | 0 | 0 | 0 | 0 | 0 | 0 | 0 | 0 | 0 | 0 |
| Unwanted plants | | | | | | | | | | | | | | | |
| *Avena fatua* | 90 | 58 | 59 | 97 | 66 | 62 | 91 | 57 | 60 | — | — | — | — | — | — |
| *Galium aparine* | 84 | 100 | 90 | 90 | 100 | 100 | 86 | 100 | 100 | 100 | 100 | 100 | 100 | 100 | 100 |
| *Stellaria media* | 75 | 100 | 78 | 77 | 100 | 86 | 90 | 100 | 100 | 100 | 100 | 100 | 100 | 100 | 100 |

0 = no damage
100 = complete destruction

| Active ingredient | III+VII+XIII | | | III+VII+XIV | | | III+VII+XV | | | III+VII+XVI | | | III+VII+XVII | | |
|---|---|---|---|---|---|---|---|---|---|---|---|---|---|---|---|
| kg/ha | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 0 | 5 | 0 | 0 | 0 | 0 | 0 | 0 | 0 | 0 | 0 | 0 | 0 | 0 |
| Hordeum vulgare | 0 | 0 | 7 | 0 | 0 | 0 | 0 | 0 | 0 | 0 | 0 | 0 | 0 | 0 | 0 |
| Secale cereale | 0 | 0 | 10 | 0 | 0 | 0 | 0 | 0 | 0 | 0 | 0 | 0 | 0 | 0 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 94 | 90 | 100 | 98 | 90 | 100 | 100 | 100 | 100 | 100 | 87 |
| Stellaria media | 100 | 100 | 100 | 100 | 100 | 98 | 100 | 100 | 97 | 100 | 100 | 100 | 100 | 100 | 90 |

0 = no damage
100 = complete destruction

| Active ingredient | III+VIII+XI | | | III+VIII+XII | | | III+VIII+XIII | | | III+VIII+XIV | | | III+VIII+XV | | |
|---|---|---|---|---|---|---|---|---|---|---|---|---|---|---|---|
| kg/ha | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 10 | 0 | 0 | 10 | 0 | 0 | 10 | 5 | 0 | 10 | 0 | 0 | 10 | 0 |
| Hordeum vulgare | 0 | 10 | 0 | 0 | 10 | 0 | 0 | 10 | 7 | 0 | 10 | 0 | 0 | 10 | 0 |
| Secale cereale | 0 | 20 | 0 | 0 | 20 | 0 | 0 | 20 | 10 | 0 | 20 | 0 | 0 | 20 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 100 | 100 | 100 | 100 | 100 | 100 | 88 | 100 | 100 | 90 |
| Stellaria media | 100 | 100 | 100 | 100 | 100 | 100 | 100 | 100 | 100 | 100 | 100 | 100 | 100 | 100 | 95 |

0 = no damage
100 = complete destruction

| Active ingredient | III+VIII+XVI | | | III+VIII+XVII | | | III+IX+XI | | | III+IX+XII | | | III+IX+XIII | | |
|---|---|---|---|---|---|---|---|---|---|---|---|---|---|---|---|
| kg/ha | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 10 | 0 | 0 | 10 | 0 | 0 | 0 | 0 | 0 | 0 | 0 | 0 | 0 | 5 |
| Hordeum vulgare | 0 | 10 | 0 | 0 | 10 | 0 | 0 | 0 | 0 | 0 | 0 | 0 | 0 | 0 | 7 |
| Secale cereale | 0 | 20 | 0 | 0 | 20 | 0 | 0 | 0 | 0 | 0 | 0 | 0 | 0 | 0 | 10 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 85 | 100 | 100 | 100 | 100 | 100 | 100 | 100 | 100 | 100 |
| Stellaria media | 100 | 100 | 100 | 100 | 100 | 95 | 100 | 100 | 100 | 100 | 100 | 100 | 100 | 100 | 100 |

0 = no damage
100 = complete destruction

| Active ingredient | III+IX+XIV | | | III+IX+XV | | | III+IX+XVI | | | III+IX+XVII | | | III+X+XI | | |
|---|---|---|---|---|---|---|---|---|---|---|---|---|---|---|---|
| kg/ha | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 |
| Unwanted plants | | | | | | | | | | | | | | | |
| Avena fatua | — | — | — | — | — | — | — | — | — | — | — | — | — | — | — |
| Galium aparine | 100 | 100 | 93 | 100 | 100 | 90 | 100 | 100 | 100 | 100 | 100 | 90 | 100 | 100 | 100 |
| Stellaraia media | 100 | 100 | 100 | 100 | 100 | 86 | 100 | 100 | 94 | 100 | 100 | 86 | 100 | 100 | 100 |

0 = no damage
100 = complete destruction

| Active Ingredient | III+X+XII | | | III+X+XIII | | | III+X+XIV | | | III+X+XV | | | III+X+XVI | | |
|---|---|---|---|---|---|---|---|---|---|---|---|---|---|---|---|
| kg/ha | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 0 | 0 | 0 | 0 | 5 | 0 | 0 | 0 | 0 | 0 | 0 | 0 | 0 | 0 |
| Hordeum vulgare | 0 | 0 | 0 | 0 | 0 | 7 | 0 | 0 | 0 | 0 | 0 | 0 | 0 | 0 | 0 |
| Secale cereale | 0 | 0 | 0 | 0 | 0 | 10 | 0 | 0 | 0 | 0 | 0 | 0 | 0 | 0 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 100 | 100 | 100 | 98 | 100 | 100 | 100 | 100 | 100 | 100 |

-continued

| Active Ingredient kg/ha | III+X+XII | | | III+X+XIII | | | III+X+XIV | | | III+X+XV | | | III+X+XVI | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Stellaria media | 100 | 100 | 100 | 100 | 100 | 100 | 100 | 100 | 100 | 100 | 100 | 96 | 100 | 100 | 100 |

0 = no damage
100 = complete destruction

| Active ingredient kg/ha | III+X+XVII | | | IV+VII+XI | | | IV+VII+XII | | | IV+VII+XIII | | | IV+VII+XIV | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 0 | 0 | 0 | 0 | 0 | 0 | 0 | 0 | 0 | 0 | 5 | 0 | 0 | 0 |
| Hordeum vulgare | 0 | 0 | 0 | 0 | 0 | 0 | 0 | 0 | 0 | 0 | 0 | 7 | 0 | 0 | 0 |
| Secale cereale | 0 | 0 | 0 | 0 | 0 | 0 | 0 | 0 | 0 | 0 | 0 | 10 | 0 | 0 | 0 |
| Unwanted plants | | | | | | | | | | | | | | | |
| Avena fatua | — | — | — | — | — | — | — | — | — | — | — | — | — | — | — |
| Galium aparine | 100 | 100 | 97 | 100 | 100 | 100 | 100 | 100 | 100 | 100 | 100 | 100 | 100 | 100 | 100 |
| Stellaria media | 100 | 100 | 97 | 100 | 100 | 100 | 100 | 100 | 100 | 100 | 100 | 100 | 100 | 100 | 91 |

0 = no damage
100 = complete destruction

| Active ingredient kg/ha | IV+VII+XV | | | IV+VII+XVI | | | IV+VII+XVII | | | IV+VIII+XI | | | IV+VIII+XII | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 0 | 0 | 0 | 0 | 0 | 0 | 0 | 0 | 0 | 10 | 0 | 0 | 10 | 0 |
| Hordeum vulgare | 0 | 0 | 0 | 0 | 0 | 0 | 0 | 0 | 0 | 0 | 10 | 0 | 0 | 10 | 0 |
| Secale cereale | 0 | 0 | 0 | 0 | 0 | 0 | 0 | 0 | 0 | 0 | 20 | 0 | 0 | 20 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 100 | 100 | 100 | 92 | 100 | 100 | 100 | 100 | 100 | 100 |
| Stellaria media | 100 | 100 | 85 | 100 | 100 | 96 | 100 | 100 | 81 | 100 | 100 | 100 | 100 | 100 | 100 |

0 = no damage
100 = complete destruction

| Active ingredient kg/ha | IV+VIII+XIII | | | IV+VIII+XIV | | | IV+VII+XV | | | IV+VIII+XVI | | | IV+VIII+XVII | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 10 | 5 | 0 | 10 | 0 | 0 | 10 | 0 | 0 | 10 | 0 | 0 | 10 | 0 |
| Hordeum vulgare | 0 | 10 | 7 | 0 | 10 | 0 | 0 | 10 | 0 | 0 | 10 | 0 | 0 | 10 | 0 |
| Secale cereale | 0 | 20 | 10 | 0 | 20 | 0 | 0 | 20 | 0 | 0 | 20 | 0 | 0 | 20 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 92 | 100 | 100 | 91 | 100 | 100 | 100 | 100 | 100 | 89 |
| Stellaria media | 100 | 100 | 100 | 100 | 100 | 95 | 100 | 100 | 86 | 100 | 100 | 96 | 100 | 100 | 85 |

0 = no damage
100 = complete destruction

| Active ingredient kg/ha | IV+IX+XI | | | IV+IX+XII | | | IV+IX+XIII | | | IV+IX+XIV | | | IV+IX+XV | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 0 | 0 | 0 | 0 | 0 | 0 | 0 | 5 | 0 | 0 | 0 | 0 | 0 | 0 |
| Hordeum vulgare | 0 | 0 | 0 | 0 | 0 | 0 | 0 | 0 | 7 | 0 | 0 | 0 | 0 | 0 | 0 |
| Secale cereale | 0 | 0 | 0 | 0 | 0 | 0 | 0 | 0 | 10 | 0 | 0 | 0 | 0 | 0 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 100 | 100 | 100 | 100 | 100 | 100 | 96 | 100 | 100 | 96 |
| Stellaria media | 100 | 100 | 100 | 100 | 100 | 100 | 100 | 100 | 100 | 100 | 100 | 86 | 100 | 100 | 80 |

0 = no damage
100 = complete destruction

| Active ingredient | IV+IX+XVI | | | IV+IX+XVII | | | IV+X+XI | | | IV+X+XII | | | IV+X+XIII | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | | | | | | | | | | |
| Triticum aestivum | 0 | 0 | 0 | 0 | 0 | 0 | 0 | 0 | 0 | 0 | 0 | 0 | 0 | 0 | 5 |
| Hordeum vulgare | 0 | 0 | 0 | 0 | 0 | 0 | 0 | 0 | 0 | 0 | 0 | 0 | 0 | 0 | 7 |
| Secale cereale | 0 | 0 | 0 | 0 | 0 | 0 | 0 | 0 | 0 | 0 | 0 | 0 | 0 | 0 | 10 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 94 | 100 | 100 | 100 | 100 | 100 | 100 | 100 | 100 | 100 |
| Stellaria media | 100 | 100 | 100 | 100 | 100 | 84 | 100 | 100 | 100 | 100 | 100 | 100 | 100 | 100 | 100 |

0 = no damage
100 = complete destruction

| Active ingredient | IV+X+XIV | | | IV+X+XV | | | IV+X+XVI | | | IV+X+XVII | | | V+VII+XI | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | | | | | | | | | | |
| Triticum aestivum | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 100 | 100 | 100 | 100 | 100 | 100 | 98 | 100 | 100 | 100 |
| Stellaria media | 100 | 100 | 92 | 100 | 100 | 82 | 100 | 100 | 91 | 100 | 100 | 80 | 100 | 100 | 100 |

0 = no damage
100 = complete destruction

| Active ingredient | V+VII+XII | | | V+VII+XIII | | | V+VII+XIV | | | V+VII+XV | | | V+VII+XVI | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | | | | | | | | | | |
| Triticum aestivum | 0 | 0 | 0 | 0 | 0 | 5 | 0 | 0 | 0 | 0 | 0 | 0 | 0 | 0 | 0 |
| Hordeum vulgare | 0 | 0 | 0 | 0 | 0 | 7 | 0 | 0 | 0 | 0 | 0 | 0 | 0 | 0 | 0 |
| Secale cereale | 0 | 0 | 0 | 0 | 0 | 10 | 0 | 0 | 0 | 0 | 0 | 0 | 0 | 0 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 100 | 100 | 100 | 98 | 100 | 100 | 97 | 100 | 100 | 100 |
| Stellaria media | 100 | 100 | 100 | 100 | 100 | 100 | 100 | 100 | 100 | 100 | 100 | 95 | 100 | 100 | 100 |

0 = no damage
100 = complete destruction

| Active ingredient | V+VII+XVII | | | V+VIII+XI | | | V+VIII+XII | | | V+VIII+XIII | | | V+VIII+XIV | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | | | | | | | | | | |
| Triticum aestivum | 0 | 0 | 0 | 0 | 10 | 0 | 0 | 10 | 0 | 0 | 10 | 5 | 0 | 10 | 0 |
| Hordeum vulgare | 0 | 0 | 0 | 0 | 10 | 0 | 0 | 10 | 0 | 0 | 10 | 7 | 0 | 10 | 0 |
| Secale cereale | 0 | 0 | 0 | 0 | 20 | 0 | 0 | 20 | 0 | 0 | 20 | 10 | 0 | 20 | 0 |
| Unwanted plants | | | | | | | | | | | | | | | |
| Avena fatua | — | — | — | — | — | — | — | — | — | — | — | — | — | — | — |
| Galium aparine | 100 | 100 | 89 | 100 | 100 | 100 | 100 | 100 | 100 | 100 | 100 | 96 | 100 | 100 | 97 |
| Stellaria media | 100 | 100 | 88 | 100 | 100 | 100 | 100 | 100 | 100 | 100 | 100 | 100 | 100 | 100 | 100 |

0 = no damage
100 = complete destruction

| Active ingredient | V+VIII+XVII | | | V+IX+XI | | | V+IX+XII | | | V+IX+XIII | | | V+IX+XIV | | |
|---|---|---|---|---|---|---|---|---|---|---|---|---|---|---|---|
| kg/ha | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 | 1<br>0.25<br>0.25 | 0.25<br>1<br>0.25 | 0.25<br>0.25<br>1 |
| Crop plants | | | | | | | | | | | | | | | |
| Triticum aestivum | 0 | 10 | 0 | 0 | 0 | 0 | 0 | 0 | 0 | 0 | 0 | 5 | 0 | 0 | 0 |
| Hordeum vulgare | 0 | 10 | 0 | 0 | 0 | 0 | 0 | 0 | 0 | 0 | 0 | 7 | 0 | 0 | 0 |
| Secale cereale | 0 | 20 | 0 | 0 | 0 | 0 | 0 | 0 | 0 | 0 | 0 | 10 | 0 | 0 | 0 |
| Unwanted plants | | | | | | | | | | | | | | | |
| Avena fatua | — | — | — | — | — | — | — | — | — | — | — | — | — | — | — |
| Galium aparine | 100 | 100 | 94 | 100 | 100 | 100 | 100 | 100 | 100 | 100 | 100 | 100 | 100 | 100 | 100 |

-continued

| Active ingredient kg/ha | V+VIII+XVII | | | V+IX+XI | | | V+IX+XII | | | V+IX+XIII | | | V+IX+XIV | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Stellaria media | 100 | 100 | 98 | 100 | 100 | 100 | 100 | 100 | 100 | 100 | 100 | 100 | 100 | 100 | 100 |

0 = no damage
100 = complete destruction

| Active ingredient kg/ha | V+IX+XV | | | V+IX+XVI | | | V+IX+XVII | | | III+XVIII+XI | | | III+XVIII+XII | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 0 | 0 | 0 | 0 | 0 | 0 | 0 | 0 | 0 | 0 | 0 | 0 | 10 | 0 |
| Hordeum vulgare | 0 | 0 | 0 | 0 | 0 | 0 | 0 | 0 | 0 | 0 | 0 | 0 | 0 | 5 | 0 |
| Secale cereale | 0 | 0 | 0 | 0 | 0 | 0 | 0 | 0 | 0 | 0 | 0 | 0 | 0 | 8 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 100 | 100 | 100 | 100 | 100 | 100 | 98 | 100 | 100 | 100 |
| Stellaria media | 100 | 100 | 91 | 100 | 100 | 100 | 100 | 100 | 100 | 100 | 100 | 90 | 100 | 100 | 100 |

0 = no damage
100 = complete destruction

| Active ingredient kg/ha | III+XVIII+XIII | | | III+XVII+XIV | | | III+XVIII+XV | | | III+XVIII+XVI | | | III+XVIII+XVII | | |
|---|---|---|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 | 0.25 | 0.25 | 1 |
| Crop plants | | | | | | | | | | | | | | | |
| Triticum aestivum | 0 | 10 | 5 | 0 | 10 | 0 | 0 | 10 | 0 | 0 | 10 | 0 | 0 | 10 | 0 |
| Hordeum vulgare | 0 | 5 | 7 | 0 | 5 | 0 | 0 | 5 | 0 | 0 | 5 | 0 | 0 | 5 | 0 |
| Secale cereale | 0 | 8 | 10 | 0 | 8 | 0 | 0 | 8 | 0 | 0 | 8 | 0 | 0 | 8 | 0 |
| Unwanted plants | | | | | | | | | | | | | | | |
| Avena fatua | — | — | — | — | — | — | — | — | — | — | — | — | — | — | — |
| Galium aparine | 100 | 100 | 100 | 100 | 100 | 87 | 100 | 100 | 85 | 100 | 100 | 100 | 100 | 100 | 80 |
| Stellaria media | 100 | 100 | 100 | 100 | 100 | 98 | 100 | 100 | 95 | 100 | 100 | 94 | 100 | 100 | 86 |

0 = no damage
100 = complete destruction

| Active ingredient kg/ha | V+X+XI | | | V+X+XII | | | V+X+XIII | | | X+X+XIV | | |
|---|---|---|---|---|---|---|---|---|---|---|---|---|
| | 1 | 0.25 | 0.25 | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 | 0.25 | 0.25 | 1 |
| Crop plants | | | | | | | | | | | | |
| Triticum aestivum | 0 | 0 | 0 | 0 | 0 | 0 | 0 | 0 | 5 | 0 | 0 | 0 |
| Hordeum vulgare | 0 | 0 | 0 | 0 | 0 | 0 | 0 | 0 | 7 | 0 | 0 | 0 |
| Secale cereale | 0 | 0 | 0 | 0 | 0 | 0 | 0 | 0 | 10 | 0 | 0 | 0 |
| Unwanted plants | | | | | | | | | | | | |
| Avena fatua | — | — | — | — | — | — | — | — | — | — | — | — |
| Galium aparine | 100 | 100 | 100 | 100 | 100 | 100 | 100 | 100 | 100 | 95 | 100 | 100 |
| Stellaria media | 100 | 100 | 100 | 100 | 100 | 100 | 100 | 100 | 100 | 100 | 100 | 100 |

0 = no damage
100 = complete destruction

| Active ingredient kg/ha | V+X+XV | | | V+X+XVI | | | V+X+XVII | | |
|---|---|---|---|---|---|---|---|---|---|
| | 1 | 0.25 | 0.25 | 1 | 0.25 | 0.25 | 1 | 0.25 | 0.25 |
| | 0.25 | 1 | 0.25 | 0.25 | 1 | 0.25 | 0.25 | 1 | 0.25 |
| | 0.25 | 0.25 | 1 | 0.25 | 0.25 | 1 | 0.25 | 0.25 | 1 |
| Crop plants | | | | | | | | | |
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Unwanted plants | | | | | | | | | |
| Avena fatua | — | — | — | — | — | — | — | — | — |
| Galium aparine | 100 | 100 | 100 | 100 | 100 | 100 | 100 | 100 | 95 |
| Stellaria media | 100 | 100 | 98 | 100 | 100 | 100 | 100 | 100 | 92 |

0 = no damage
100 = complete destruction

EXAMPLE 8

In the greenhouse, various plants were treated at a growth height of from 2 to 20 cm with the following amounts of the following individual active ingredients and compositions thereof:

I 1,2-dimethyl-3,5-diphenylpyrazolium methyl sulfate
III 3-isopropyl-2,1,3-benzothiadiazinone-(4)-2,2-dioxide
IV 3-isopropyl-2,1,3-benzothiadiazinone-(4)-2,2-dioxide, sodium salt
V 3-isopropyl-2,1,3-benzothiadiazinone-(4)-2,2-dioxide, dimethylamine salt
VI 3-isopropyl-2,1,3-benzothiadiazinone-(4)-2,2-dioxide, diethanolamine salt
XI α-(2-methyl-4-chlorophenoxy)-propionic acid, sodium salt
XII α-(2,4-dichlorophenoxy)-propionic acid, dimethylamine salt
XIV 2-methyl-4-chlorophenoxyacetic acid, dimethylamine salt
XV 2,4-dichlorophenoxyacetic acid, dimethylamine salt
XVI 2,4,5-trichlorophenoxyacetic acid, isooctyl ester each of compounds I to VI at rates of 0.5 and 1.5 kg/ha, and each of compounds XI to XVI at rates of 0.25 and 1.5 kg/ha; I + III + XV + XIV, I + IV + XV + XIV, I + V + XV + XIV, I + VI + XV + XIV, I + III + XV + XI, I + IV + XV + XI, I + V + XV + XI, I + VI + XV + XI, I + III + XI + XVI, I + IV + XI + XVI, I + V + XI + XVI, I + VI + XI + XVI, I + III + XV + XVI, I + IV + XV + XVI, I + V + XV + XVI, I + VI + XV + XVI, I + VI + XIV + XVI, I + IV + XIV + XVI, I + V + XIV + XVI, I + VI + XIV + XVI, I + III + XII + XVI, I + IV + XII + XVI, I + V + XII + XVI, I + VI + XII + XVI each of these compositions at a rate of 0.5+0.5+0.25+0.25 kg/ha.

After 12 to 15 days it was ascertained that the compositions had a better herbicidal action than their components, combined with the same crop plant compatibility.

The results are given below:

| Active ingredient kg/ha | I 0.5 | I 1.5 | III 0.5 | III 1.5 | IV 0.5 | IV 1.5 | V 0.5 | V 1.5 | VI 0.5 | VI 1.5 | XI 0.25 | XI 1.5 | XII 0.25 | XII 1.5 | XIV 0.25 | XIV 1.5 | XV 0.25 | XV 1.5 | XVI 0.25 | XVI 1.5 |
|---|---|---|---|---|---|---|---|---|---|---|---|---|---|---|---|---|---|---|---|---|
| Crop plants: | | | | | | | | | | | | | | | | | | | | |
| Triticum aestivum | 0 | 0 | 0 | 0 | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 | 0 | 0 | 0 | 5 |
| Secale cereale | 0 | 0 | 0 | 0 | 0 | 0 | 0 | 0 | 0 | 0 | 0 | 0 | 0 | 0 | 0 | 0 | 0 | 0 | 0 | 7 |
| Unwanted plants: | | | | | | | | | | | | | | | | | | | | |
| Avena fatua | 35 | 80 | 0 | 0 | 0 | 0 | 0 | 0 | 0 | 0 | 0 | 0 | 0 | 5 | 0 | 0 | 0 | 0 | 0 | 0 |
| Galium aparine | 0 | 10 | 35 | 75 | 30 | 75 | 30 | 60 | 35 | 80 | 15 | 70 | 10 | 75 | 5 | 25 | 5 | 25 | 15 | 80 |
| Stellaria media | 5 | 14 | 30 | 70 | 20 | 70 | 20 | 70 | 20 | 85 | 20 | 70 | 15 | 75 | 10 | 35 | 3 | 20 | 5 | 36 |

0 = no damage
100 = complete destruction

| Active ingredient kg/ha | I+III+XV+XIV 0.5+0.5+0.25+0.25 | I+IV+XV+XIV 0.5+0.5+0.25+0.25 | I+V+XV+XIV 0.5+0.5+0.25+0.25 | I+VI+XV+XIV 0.5+0.5+0.25+0.25 |
|---|---|---|---|---|
| Crop plants: | | | | |
| Triticum aestivum | 0 | 0 | 0 | 0 |
| Hordeum vulgare | 0 | 0 | 0 | 0 |
| Secale cereale | 0 | 0 | 0 | 0 |
| Unwanted plants: | | | | |
| Avena fatua | 80 | 82 | 81 | 83 |
| Galium aparine | 85 | 80 | 79 | 84 |
| Stellaria media | 88 | 77 | 78 | 76 |

0 = no damage
100 = complete destruction

| Active ingredient kg/ha | I+III+XV+XI 0.5+0.5+0.25+0.25 | I+IV+XV+XI 0.5+0.5+0.25+0.25 | I+V+XV+XI 0.5+0.5+0.25+0.25 | I+VI+XV+XI 0.5+0.5+0.25+0.25 |
|---|---|---|---|---|
| Crop plants: | | | | |
| Triticum aestivum | 0 | 0 | 0 | 0 |
| Hordeum vulgare | 0 | 0 | 0 | 0 |
| Secale cereale | 0 | 0 | 0 | 0 |
| Unwanted plants: | | | | |
| Avena fatua | 81 | 80 | 82 | 83 |
| Galium aparine | 94 | 90 | 91 | 95 |
| Stellaria media | 98 | 87 | 89 | 88 |

0 = no damage
100 = complete destruction

| Active ingredient kg/ha | I+III+XI+XVI 0.5+0.5+0.25+0.25 | I+IV+XI+XVI 0.5+0.5+0.25+0.25 | I+V+XI+XVI 0.5+0.5+0.25+0.25 | I+VI+XI+XVI 0.5+0.5+0.25+0.25 |
|---|---|---|---|---|
| Crop plants: | | | | |
| Triticum aestivum | 0 | 0 | 0 | 0 |
| Hordeum vulgare | 0 | 0 | 0 | 0 |
| Secale cereale | 0 | 0 | 0 | 0 |

-continued

| Active ingredient kg/ha | I+III+XI+XVI 0.5+0.5+0.25+0.25 | I+IV+XI+XVI 0.5+0.5+0.25+0.25 | I+V+XI+XVI 0.5+0.5+0.25+0.25 | I+VI+XI+XVI 0.5+0.5+0.25+0.25 |
|---|---|---|---|---|
| Unwanted plants: | | | | |
| Avena fatua | 80 | 81 | 80 | 83 |
| Galium aparine | 100 | 100 | 100 | 100 |
| Stellaria media | 100 | 92 | 90 | 93 |

0 = no damage
100 = complete destruction

| Active ingredient kg/ha | I+III+XV+XVI 0.5+0.5+0.25+0.25 | I+IV+XV+XVI 0.5+0.5+0.25+0.25 | I+V+XV+XVI 0.5+0.5+0.25+0.25 | I+VI+XV+XVI 0.5+0.5+0.25+0.25 |
|---|---|---|---|---|
| Crop plants: | | | | |
| Triticum aestivum | 0 | 0 | 0 | 0 |
| Hordeum vulgare | 0 | 0 | 0 | 0 |
| Secale cereale | 0 | 0 | 0 | 0 |
| Unwanted plants: | | | | |
| Avena fatua | 81 | 80 | 82 | 79 |
| Galium aparine | 95 | 90 | 88 | 96 |
| Stellaria media | 83 | 73 | 75 | 74 |

0 = no damage
100 = complete destruction

| Active ingredient kg/ha | I+III+XIV+XVI 0.5+0.5+0.25+0.25 | I+IV+XIV+XVI 0.5+0.5+0.25+0.25 | I+V+XIV+XVI 0.5+0.5+0.25+0.25 | I+VI+XIV+XVI 0.5+0.5+0.25+0.25 |
|---|---|---|---|---|
| Crop plants: | | | | |
| Triticum aestivum | 0 | 0 | 0 | 0 |
| Hordeum vulgare | 0 | 0 | 0 | 0 |
| Secale cereale | 0 | 0 | 0 | 0 |
| Unwanted plants: | | | | |
| Avena fatua | 80 | 79 | 89 | 80 |
| Galium aparine | 96 | 91 | 89 | 94 |
| Stellaria media | 90 | 80 | 82 | 79 |

0 = no damage
100 = complete destruction

| Active ingredient kg/ha | I+III+XII+XVI 0.5+0.5+0.25+0.25 | I+IV+XII+XVI 0.5+0.5+0.25+0.25 | I+V+XII+XVI 0.5+0.5+0.25+0.25 | I+VI+XII+XVI 0.5+0.5+0.25+0.25 |
|---|---|---|---|---|
| Crop plants: | | | | |
| Triticum aestivum | 0 | 0 | 0 | 0 |
| Hordeum vulgare | 0 | 0 | 0 | 0 |
| Secale cereale | 0 | 0 | 0 | 0 |
| Unwanted plants: | | | | |
| Avena fatua | 80 | 82 | 80 | 81 |
| Galium aparine | 95 | 96 | 94 | 98 |
| Stellaria media | 95 | 84 | 85 | 83 |

0 = no damage
100 = complete destruction

What we claim is:
1. A herbicide composition consisting essentially of an inert carrier and a herbicidally effective amount of a mixture of
a. a compound of the formula

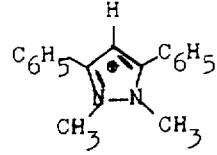

in which R denotes lower alkoxy or phenyl which may be substituted by lower alkyl, and
b. a compound of the formula

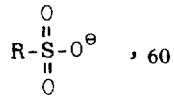

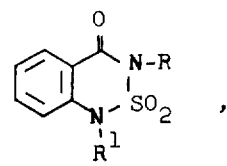

in which R denotes lower alkyl and $R^1$ denotes hydrogen, or an alkali metal, alkaline earth or substituted amine salt of said compound (b) in a weight ratio of a:b of 5:1 to 1:5.

2. A herbicide composition as claimed in claim 1, in which compound a is 1,2-dimethyl-3,5-diphenylpyrazolium methyl sulfate or 1,2-dimethyl-3,5-diphenylpyrazolium-p-tolyl sulfonate.

3. A herbicide composition as claimed in claim 1 wherein said salt of compound b is the ammonium, sodium, potassium, lithium, calcium, magnesium, ethylamine, dimethylamine, diethylamine, diethanolamine, ethanolamine, dimethylethanolamine or trimethylamine salt.

4. A herbicide composition as claimed in claim 1 in which R of compound *b* is isopropyl.

* * * * *